(12) United States Patent
Kathirgamanathan et al.

(10) Patent No.: US 8,883,325 B2
(45) Date of Patent: *Nov. 11, 2014

(54) ELECTROLUMINESCENT DEVICE USING AZOMETHINE-LITHIUM-COMPLEX AS ELECTRON INJECTION LAYER

(75) Inventors: Poopathy Kathirgamanathan, North Harrow (GB); Yun Fu Chan, Cleveland (GB)

(73) Assignee: Merck Patent GmbH, Darmstadt (DE)

( * ) Notice: Subject to any disclaimer, the term of this patent is extended or adjusted under 35 U.S.C. 154(b) by 187 days.

This patent is subject to a terminal disclaimer.

(21) Appl. No.: 13/458,030

(22) Filed: Apr. 27, 2012

(65) Prior Publication Data

US 2012/0205638 A1    Aug. 16, 2012

Related U.S. Application Data

(62) Division of application No. 12/521,334, filed as application No. PCT/GB2007/050769 on Dec. 19, 2007, now abandoned.

(30) Foreign Application Priority Data

Dec. 29, 2006 (GB) .................... 0625865.1

(51) Int. Cl.
  H01L 51/50    (2006.01)
  C09K 11/06    (2006.01)
  C07F 1/02     (2006.01)
  H01B 1/12     (2006.01)
  C07C 251/24   (2006.01)
  C07C 255/61   (2006.01)
  H05B 33/14    (2006.01)
  H01L 51/00    (2006.01)

(52) U.S. Cl.
  CPC ........ H05B 33/14 (2013.01); *C09K 2211/1037* (2013.01); C07C 251/24 (2013.01); *C09K 2211/185* (2013.01); *C09K 2211/1007* (2013.01); *C09K 2211/1059* (2013.01); *H01L 51/005* (2013.01); C07C 255/61 (2013.01); *C09K 2211/1011* (2013.01); *C09K 2211/1088* (2013.01); *C09K 2211/1029* (2013.01); *C09K 2211/1044* (2013.01); *C09K 2211/181* (2013.01); C09K 11/06 (2013.01); *C09K 2211/1014* (2013.01); H01L 51/0077 (2013.01); *H01L 51/5092* (2013.01); *H01L 51/0072* (2013.01); *C09K 2211/1092* (2013.01); *Y10S 428/917* (2013.01)
  USPC ...... 428/690; 428/917; 257/40; 257/E51.018; 252/500; 252/301.16; 252/301.33; 564/270; 548/193

(58) Field of Classification Search
  None
  See application file for complete search history.

(56) References Cited

U.S. PATENT DOCUMENTS

| 4,356,429 A | 10/1982 | Tang |
| 4,720,432 A | 1/1988 | VanSlyke et al. |
| 4,769,292 A | 9/1988 | Tang et al. |
| 5,141,671 A | 8/1992 | Bryan et al. |
| 5,432,014 A | 7/1995 | Sano et al. |
| 6,208,075 B1 | 3/2001 | Hung et al. |
| 6,316,130 B1 | 11/2001 | Heuer et al. |
| 6,396,209 B1 * | 5/2002 | Kido et al. ..................... 313/504 |

(Continued)

FOREIGN PATENT DOCUMENTS

EP    0891121 A1    1/1999
EP    1029909 A1    8/2000

(Continued)

OTHER PUBLICATIONS

Olekhnovich et al., Zhurnal Organicheskoi Khimii, vol. IX, issue 8, 1973, pp. 1724-1730, Ed. "Nauka", Moskow, RU.

(Continued)

*Primary Examiner* — Andrew K Bohaty
(74) *Attorney, Agent, or Firm* — Drinker Biddle & Reath LLP

(57)     ABSTRACT

In OLEDs, improved efficiency is obtained by compounds which can form inter alia electron injection layers of the formula (I)

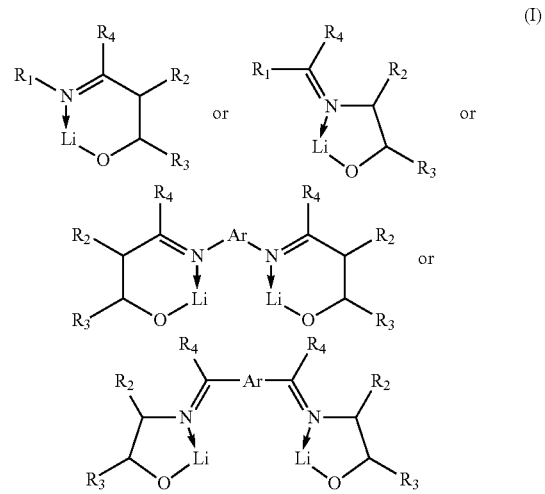

wherein
$R_1$ is a 1-5 ring aryl (including polycyclic), aralkyl or heteroaryl group which is optionally substituted with one or more $C_1$-$C_4$ alkyl, alkoxy or cyano;
$R_2$ and $R_3$ together form a 1-5 ring aryl (including polycyclic), aralkyl or heteroaryl group which is optionally substituted with $C_1$-$C_4$ alkyl, alkoxy or cyano;
$R_4$ is hydrogen, $C_1$-$C_4$ alkyl or aryl; and
Ar is monocyclic, bicyclic or tricyclic aryl or heteroaryl which is optionally substituted with one or more $C_1$-$C_4$- alkyl or alkoxy groups, or an oligomer thereof.

30 Claims, 7 Drawing Sheets

(56) References Cited

U.S. PATENT DOCUMENTS

| | | |
|---|---|---|
| 6,885,149 B2 | 4/2005 | Parthasarathy et al. |
| 7,114,638 B2 | 10/2006 | Vaynshteyn et al. |
| 8,507,896 B2 * | 8/2013 | Kathirgamanathan et al. .. 257/40 |
| 2001/0014391 A1 | 8/2001 | Forrest et al. |
| 2003/0148142 A1 * | 8/2003 | Fryd et al. ................. 428/690 |
| 2004/0180234 A1 | 9/2004 | Lee et al. |
| 2004/0191565 A1 * | 9/2004 | Takahashi ................. 428/690 |
| 2005/0129978 A1 | 6/2005 | Nakashima et al. |
| 2006/0003089 A1 | 1/2006 | Kathirgamanathan |
| 2006/0040131 A1 * | 2/2006 | Klubek et al. ............. 428/690 |
| 2006/0040139 A1 | 2/2006 | Herron et al. |
| 2006/0079004 A1 | 4/2006 | Werner et al. |
| 2006/0286402 A1 | 12/2006 | Begley et al. |
| 2010/0327264 A1 | 12/2010 | Kathirgamanathan et al. |

FOREIGN PATENT DOCUMENTS

| | | | |
|---|---|---|---|
| WO | WO-00/32717 A1 | 6/2000 | |
| WO | WO-03/006573 A1 | 1/2003 | |
| WO | WO-03/007663 A1 | 1/2003 | |
| WO | WO-03067679 A1 | 8/2003 | |
| WO | WO-2004/050793 A1 | 6/2004 | |
| WO | WO-2004/058783 A1 | 7/2004 | |
| WO | WO-2004/058913 A1 | 7/2004 | |
| WO | WO-2004/084325 A1 | 9/2004 | |
| WO | WO-2005043641 A1 | 5/2005 | |
| WO | WO-2005/080526 A2 | 9/2005 | |
| WO | WO-2006/016193 A1 | 2/2006 | |
| WO | WO-2006/024878 A1 | 3/2006 | |
| WO | WO-2006/040593 A1 | 4/2006 | |
| WO | WO-2006061594 A1 | 6/2006 | |
| WO | WO-2006/090098 A1 | 8/2006 | |
| WO | WO-2006087521 A1 | 8/2006 | |
| WO | WO 2006097717 A1 * | 9/2006 | |
| WO | WO-2007052083 A2 | 5/2007 | |
| WO | WO-2008078114 A1 | 7/2008 | |

OTHER PUBLICATIONS

Olekhnovich, L.P., et al., "Benzenoid—Quinoid Tautomerism of Azomethines and Their Structural Analogs", Rostov-on-Son State University, Translated from Ahurnal Organicheskoi Khimii, vol. 9, No. 8, pp. 1746-1751, Aug. 1973.

* cited by examiner

Fluorescent Green: Device Performance ($\eta_p$ vs. L)
Compound A vs. LiF as an EIL ITO/ZnTpTP(20 nm)/a-NPB(50 nm)/Alq$_3$:DPQA(40 nm:0.1 nm)/Zrq$_4$(20)/EIL(0.5)/Al Fluorescent Green: Device Performance ($J_d$ vs. V)
Compound A vs. LiF as an EIL ITO/ZnTpTP(20 nm)/a-NPB(50 nm)/Alq$_3$:DPQA(40 nm:0.1 nm)/Zrq$_4$(20 nm)/EIL(0.5)/Al Blue Fluorescent Devices: Comparison of EILs Blue Fluorescent Devices: Comparison of EILs

ELECTROLUMINESCENT DEVICE USING AZOMETHINE-LITHIUM-COMPLEX AS ELECTRON INJECTION LAYER

CROSS-REFERENCE TO RELATED APPLICATIONS

This Application is a Division of application Ser. No. 12/521,334 filed on Jun. 26, 2009 which is incorporated by reference. Application Ser. No. 12/521,334 is a national stage application of Application PCT/GB2007/050769 which claims priority for Application 0625865.1 filed on Dec. 29, 2006 in the United Kingdom.

FIELD OF THE INVENTION

This invention relates to novel compounds, comprising said compounds and one or more dopants, and to their use in electro-optical or opto-electronic devices, inter alia optical light emitting devices, for example in an electron injection layer.

BACKGROUND TO THE INVENTION

Hung et al., "Recent progress of molecular organic electroluminescent materials and devices", *Materials Science and Engineering*, R 39 (2002), 143-222 disclose that bilayer cathodes for OLEDs based e.g. on a thin (0.1-1.0 nm) LiF layer between an aluminium cathode and an aluminium quinolate electron transport layer exhibit significantly improved I-V characteristics and EL efficiencies. They explain that in OLEDs, the majority carriers are holes owing to their higher mobility and smaller injection barrier. Therefore, lowering the barrier height to electron injection is especially important as it leads to a better balance of electron and hole currents and results in a dramatic increase in luminance at a fixed bias voltage. The replacement of LiF with CsF or alkaline earth fluorides is also discussed.

U.S. Pat. No. 6,885,149 (Parthasarathy et al., Princeton University) discloses that during fabrication of an OLED, an organic electron injection layer may be doped with a metal either by depositing an organic electron injection layer on an ultra-thin layer of lithium or by depositing an ultra-thin layer of lithium on an organic electron injection layer, the organic material being e.g. 2,9-dimethyl-4,7-diphenyl-1,10-phenanthroline (BCP or bathocuproine). Use of a metal doped electron injection layer is also disclosed in U.S. Pat. No. 7,114,638, the organic component of said layer being e.g. the compound shown below:

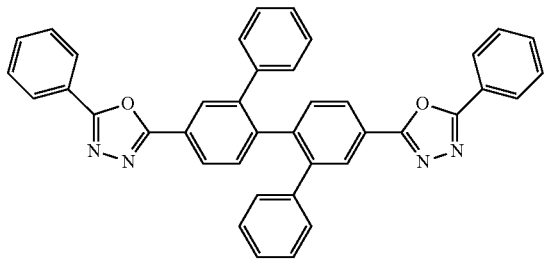 [SMILES: c1ccc(-c2nnc(-c3ccc(-c4ccc(-c5nnc(-c6ccccc6)o5)cc4-c4ccccc4)c(-c4ccccc4)c3)o2)cc1]

US-A-20060040139 (Herron et al., Du Pont) discloses the use of metal Schiff base complexes in double heterostructure OLEDs as host material in the electroluminescent layer or in the electron transport layer. The complexes are based on aluminium, scandium, yttrium or a rare earth metal and the Schiff base ligand is bivalent and is e.g. of formula:

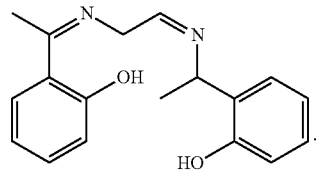 [SMILES: C/C(=N/C/C=N\C(C)c1ccccc1O)c1ccccc1O]

However, the use of metal Schiff base complexes as electron injection materials for OLEDs is neither disclosed nor suggested by Herron et al.

SUMMARY OF THE INVENTION

A problem with which invention is concerned is to provide OLEDs of improved performance. A further problem with which the invention is concerned is to provide organic materials useful as OLED layer materials or components e.g. as electron injection materials.

In one aspect, the invention provides a compound of the formula

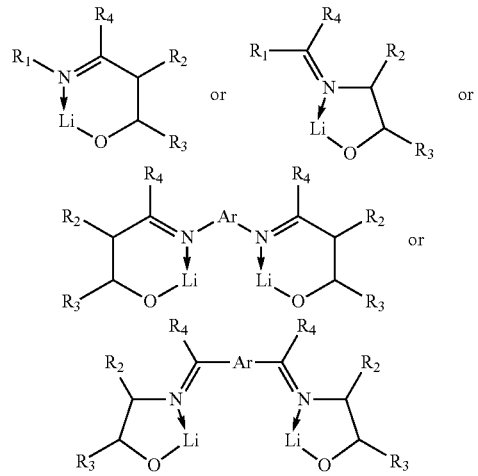

wherein
$R_1$ is a 1-5 ring aryl (including polycyclic), aralkyl or heteroaryl group which may be substituted with one or more $C_1$-$C_4$ alkyl (e.g. methyl), alkoxy (e.g. methoxy) or cyano;
$R_2$ and $R_3$ together form a 1-5 ring aryl (including polycyclic), aralkyl or heteroaryl group which may be substituted with $C_1$-$C_4$ alkyl (e.g. methyl), alkoxy or cyano;
$R_4$ is hydrogen, $C_1$-$C_4$ alkyl (e.g. methyl), aryl (e.g. phenyl or naphthyl) or heteroaryl; and
Ar is monocyclic, bicyclic or tricyclic aryl or heteroaryl which may be substituted with one or more $C_1$-$C_4$-alkyl or alkoxy groups,
or an oligomer thereof.

Compounds of the above formula in which $R_4$ is hydrogen may be made by reacting a primary aromatic or heteroaromatic amine with an aromatic or heteroaromatic aldehyde to form a Schiff base, followed by reaction of the Schiff base with a lithium compound e.g. a lithium alkoxide e.g. lithium t-butoxide. Compounds of the above formula in which $R_4$ is alkyl, acyl or heteroaryl may be made similarly starting from a secondary aromatic or heteroaromatic amine.

The compounds of the above formula have the advantage that they give comparable performance to LiF when used as an electron injection layer, or in some embodiments better performance, but do not require the severe deposition conditions associated with LiF. Embodiments of the compounds can be handled in air and can be deposited by vacuum sublimation at temperatures significantly below that required for LiF (FIG. 13) e.g. below about 250° C. In addition to vacuum sublimation, embodiments of the compounds can be deposited by the organic vapour phase deposition (OVPD) process described inter alia by Universal Display Corporation in which organic films are deposited using an inert carrier gas to transfer films of organic material onto a cooled substrate in a hot-walled, low-pressure (typically 0.1-1 Torr) chamber. The process is stated to achieve relatively high deposition rates compared to vacuum sublimation, to permit better shadow mask patterning for forming arrays of pixels and to be useful for substrates of relatively large size. They can also be deposited by organo vapour jet printing (OVJP) which produces a collimated vapour jet of organic material and carrier gas and impinges the jet onto a cooled substrate to form a well defined deposit e.g. of individual pixels, see Shtein et al., Direct Mask-Free Patterning Of Molecular Organic Semiconductors Using Organic Vapor Jet Printing, *J. Appl. Phys.*, 2004, 96(8), 4500 and WO 2005/043641 (Shtein et al.). Embodiments of the above compounds can be dissolved in organic solvents and deposited e.g. to form layers or pixels by solution coating e.g. spin coating or by ink jet printing (see WO 03/067679 and Bharathan et al., Polymer electroluminescent devices processed by inkjet printing, *Alppl Phys. Lett.*, (1998) 72(21), 2660) the contents of which are incorporated herein by reference) the good solution processing properties being a significant advantage e.g. in the manufacture of polymer OLEDs, devices based on conductive polymers e.g. PEDOT. Ink jet printing has been reported using simple organic solvents e.g. an alcohol or chloroform. Preferred ink jet printing is using the piezo variant, and suitable solvents are dichloroethylene, thrichloroethylene, xylenes, N-methyl pyrrolidones, dioxane and other high boiling ethers, dichlorobnzene and polyhydroxy compounds. Similar solvents can be used in spin coating. In some embodiments, the compounds described above may when used as electron injection layers give rise to reduced voltage drift compared to the use of inorganic electron injectors such as LiF and increased device lifetime.

The compounds whose formulae are set out above are believed from MS measurements to be capable of forming cluster compounds or oligomers in which 2-8 molecules of formula as set out above are associated e.g. in the form of trimeric, tetrameric, hexameric or octomeric oligomers. Although the invention is not dependent on the correctness of this theory, it is believed that, compounds of the invention may in some embodiments associate in trimeric units having a core structure which has alternating Li and O atoms in a 6-membered ring, and that these trimeric units may further associate in pairs. The existence of such structures in lithium quinolate has been detected by crystallography, see Begley et al., Hexakis(μ-quinolin-8-olato)hexalithium (I): a centrosymmetric doubly stacked trimer, *Acta Cryst.* (2006), E62, m1200-m1202, the disclosure of which is incorporated herein by reference. Again although the invention is not dependent on the correctness of this theory, it is believed that formation of oligomeric structures of this type imparts a greater covalent character to the Li—O bonds which may be responsible for the volatility of many of the compounds of the invention which enables them to be deposited at relatively low temperatures by vacuum sublimation. However, other structures may also be possible e.g. cubic structures.

In a further aspect, the invention provides an electro-optical or opto-electronic device having a layer comprising a compound as defined above. Such devices include OLEDs and also e.g. organic phototransistors, organic photovoltaic cells, organic photodetectors, electronic storage devices based on bistable organic molecules and photoconductive imaging members for creating electrostatic latent images.

In a yet further aspect the invention provides an optical light emitting diode device having a first electrode, a layer comprising a compound as set out above and a second electrode. The layer is in an embodiment located on the cathode and is an electron injection layer.

BRIEF DESCRIPTION OF THE DRAWINGS

Embodiments of the invention are illustrated in the accompanying drawings in which.

DESCRIPTION OF PREFERRED FEATURES

Doped Materials

Figure 1:
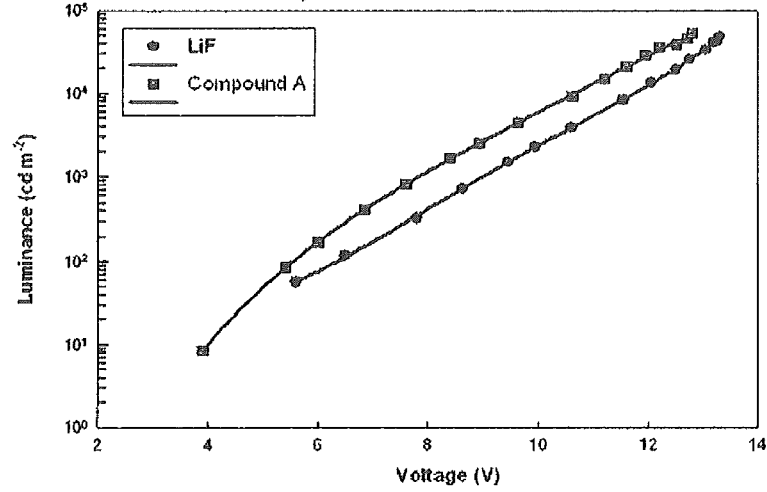
FIGS. 1-12 are graphs showing performance data for OLED devices of indicated structure.
Figure 2:
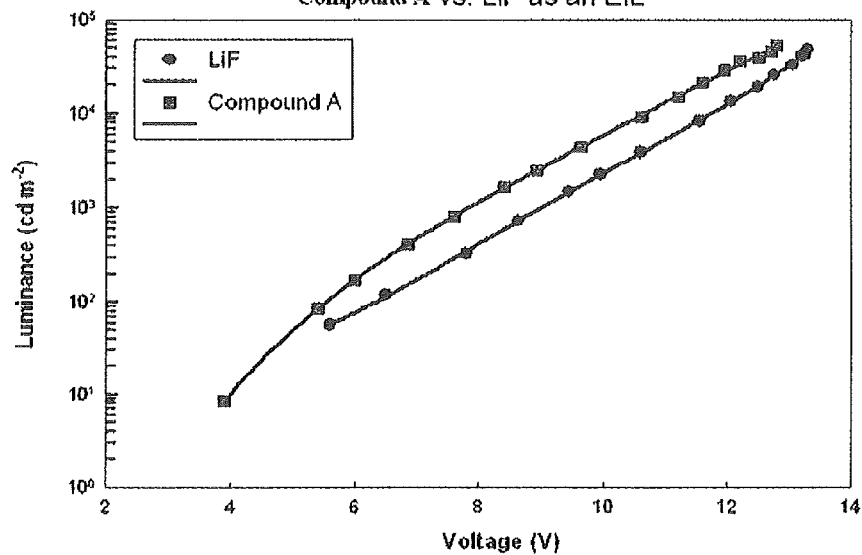
Figure 3:
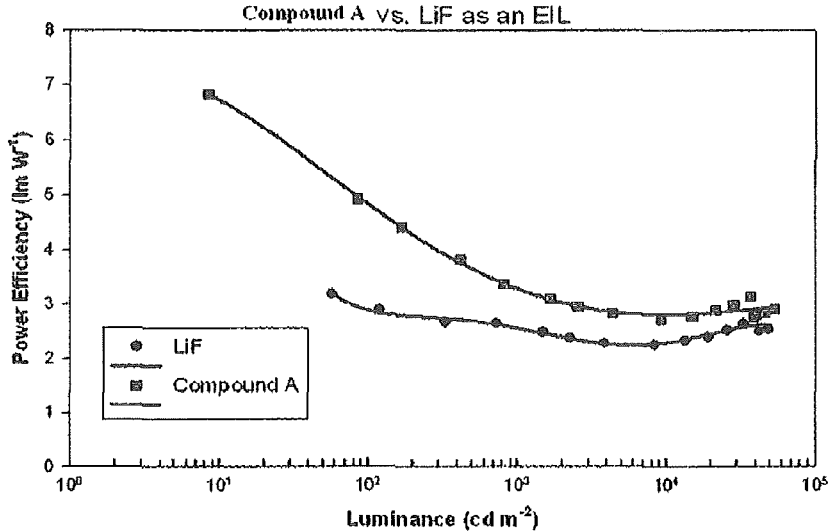
Figure 4:
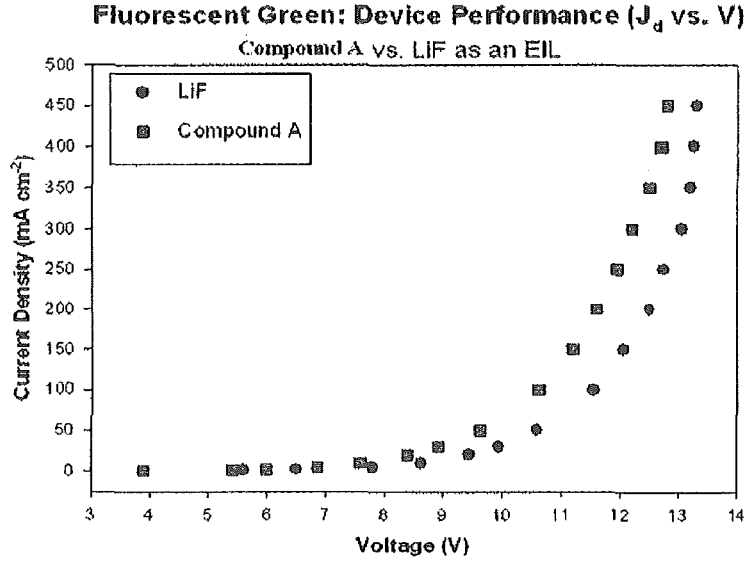
Figure 5:
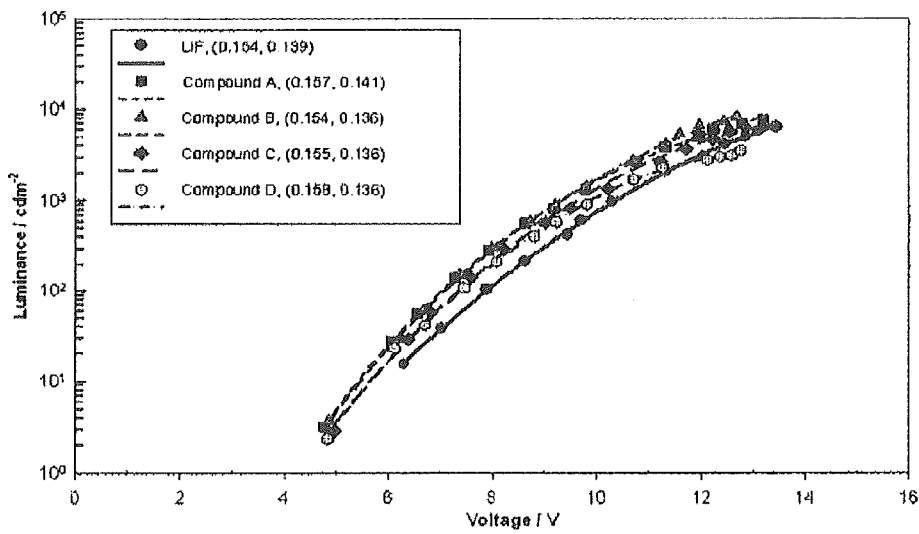
Figure 6:
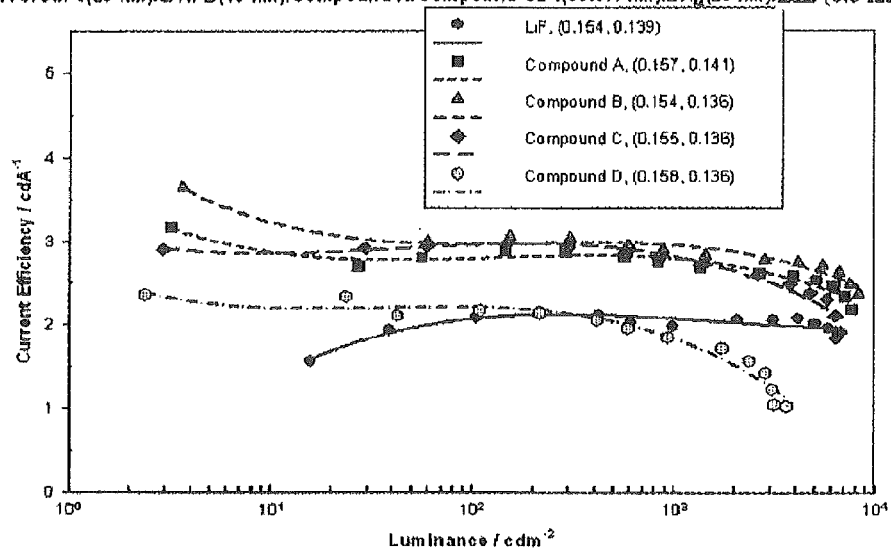
Figure 7:
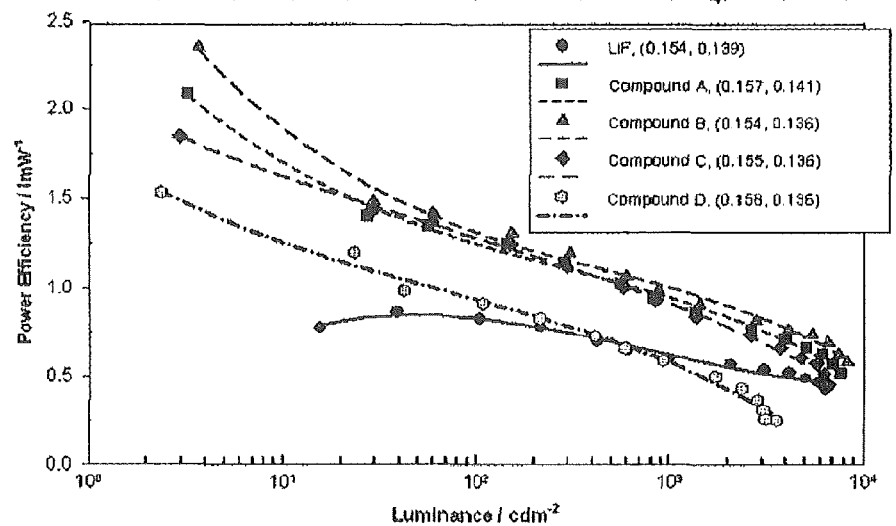
Figure 8:
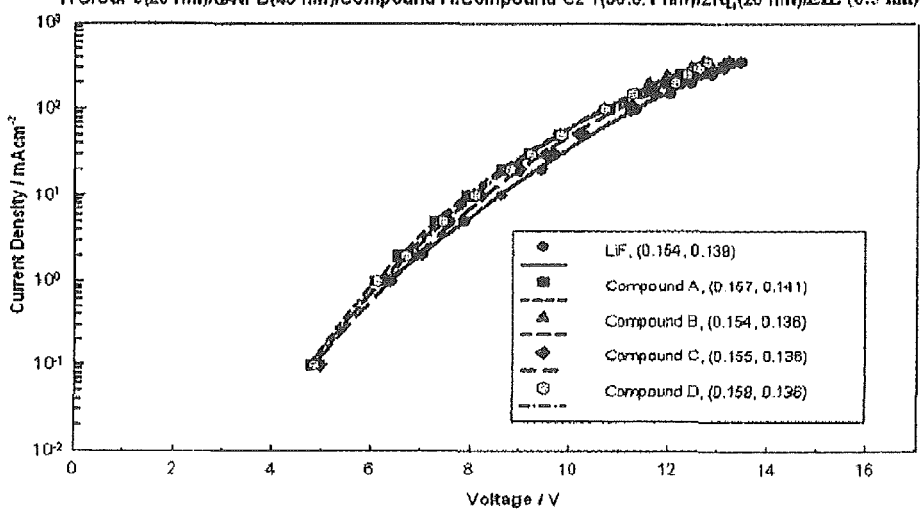
Figure 9:
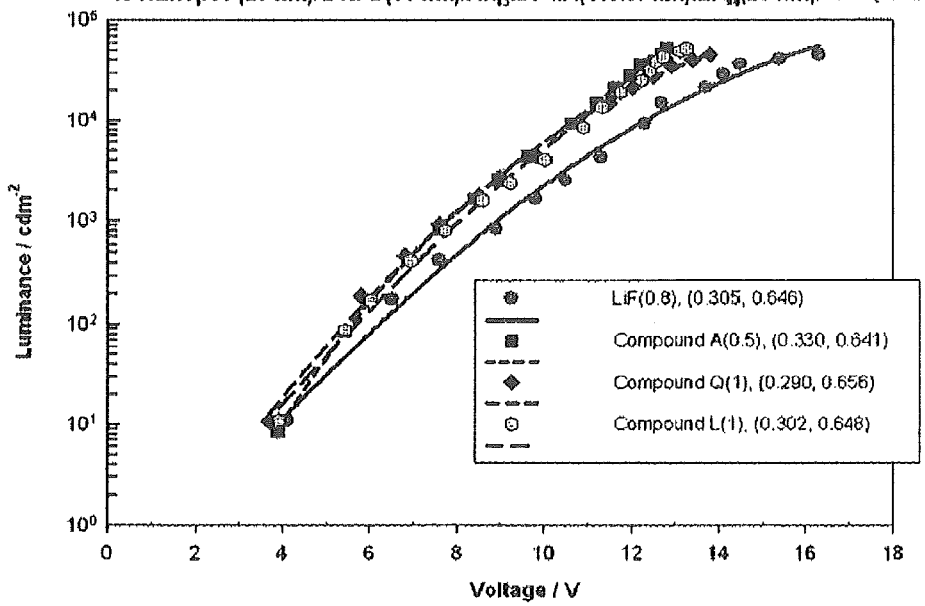
Figure 10:
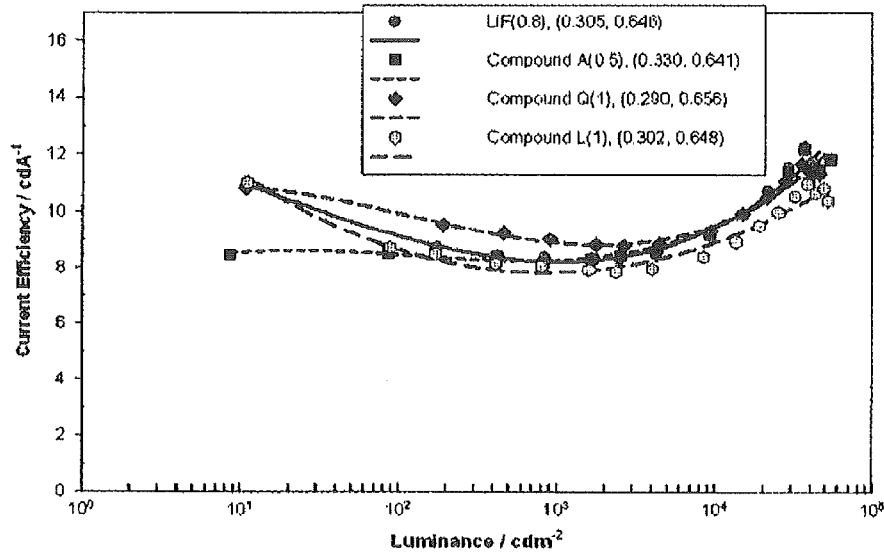
Figure 11:
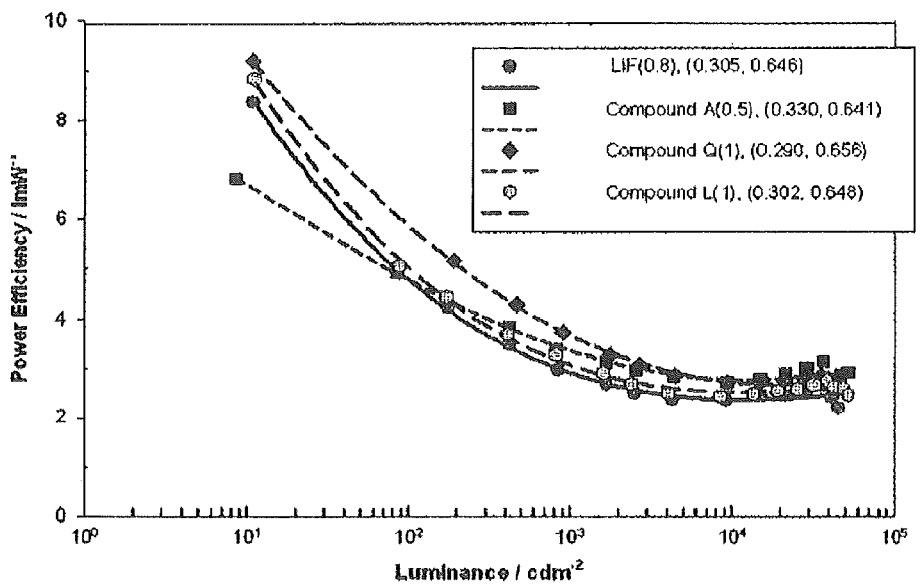
Figure 12:
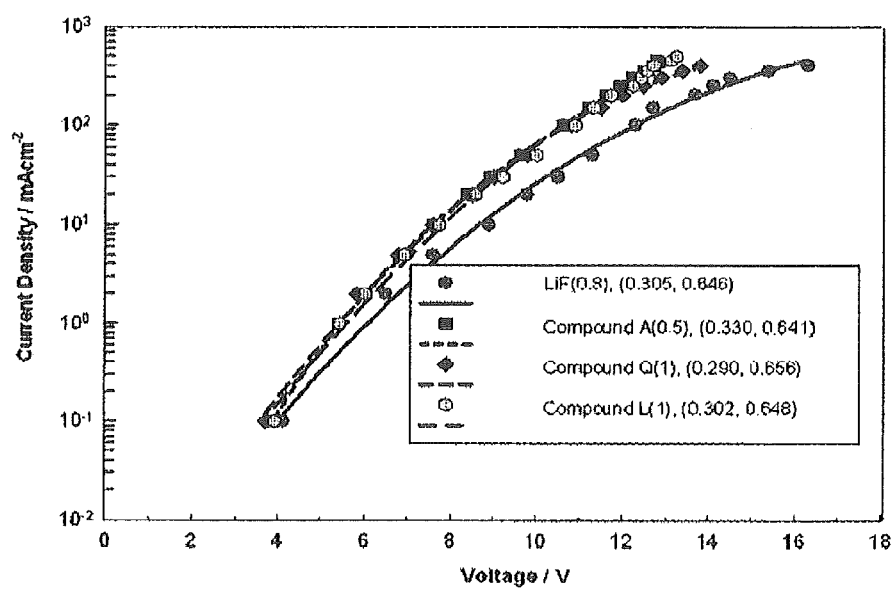

Compounds whose formulae are as set out above may be doped with a range of materials for a range of purposes.

Where they are to serve as electron injection layers they may be doped with low work function metals e.g. Li, Cs, K, Ca. Ba or complexes thereof e.g. by exposure of the compound in vacuo to vapour of the metal with which the compound is desired to be doped. For example US-A-2006/0079004 (Werner et al, the disclosure of which is incorporated herein by reference) explains that Cs is commonly used because Cs doped organic semiconductors exhibit relatively high stability. Doping by exposure of the organic semiconductor to Cs can be carried out at moderate temperatures about 300° C. using a GaCs alloy e.g. $Ga_7Cs_{11}$. They may also be mixed or doped with complexes e.g quinolates.

Compounds whose formulae are as set out above may be mixed with electron transport materials. Kulkarni et al., *Chem. Mater.* 2004, 16, 4556-4573 (the contents of which are incorporated herein by reference) have reviewed the literature concerning electron transport materials (ETMs) used to enhance the performance of organic light-emitting diodes (OLEDs). In addition to a large number of organic materials with which the present compounds can be mixed they discuss metal chelates, with which the present compounds may additionally or alternatively be mixed including aluminium quinolate, which they explain remains the most widely studied metal chelate owing to its superior properties such as high EA (~−3.0 eV; measured by the present applicants as −2.9 eV) and IP (~−5.95 eV; measured by the present applicants as about −5.7 eV), good thermal stability (Tg~172° C.) and ready deposition of pinhole-free thin films by vacuum evaporation. Aluminium quinolate remains a preferred material both for use as a host to be doped with various fluorescent materials to provide an electroluminescent layer and for use as an electron transport layer. More recently zirconium and hafnium quinolates have been disclosed as electron transport materials, see PCT/GB2007/050737 (Kathirgamanathan et al.) the contents of which are incorporated herein by reference, and the compounds whose formulae are set out above may also be mixed with zirconium or hafnium quinolate. There may also be used e.g. azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ); phenanthrolines such as 4,7-diphenyl-1,10-phenanthroline (DPA) and 2,9-dimethyl-4,7-diphenyl-1,10-phenanthroline (DDPA); and mixtures thereof.

When incorporated into electroluminescent layers, a compound of the formula set out above may serve as a host material and may be mixed or doped with a fluorescent material or with a phosphorescent material. Such materials are reviewed below in relation to the electroluminescent layer.

Cell Structure

The OLEDs of the invention are useful inter alia in flat panel displays and typically comprise an anode and a cathode between which is sandwiched a multiplicity of thin layers including an electroluminescent layer, electron injection and/or transport layer(s), hole injection and/or transport layer(s) and optionally ancillary layers. The layers are typically built up by successive vacuum vapour deposition operations, although it may be convenient to form one or more of the layers e.g. the hole injection and hole transport layers by other methods e.g. spin coating or ink jet printing.

A typical device comprises a transparent substrate on which are successively formed an anode layer, a hole injector (buffer) layer, a hole transport layer, an electroluminescent layer, an electron transport layer, an electron injection layer and an anode layer which may in turn be laminated to a second transparent substrate. Top emitting OLEDs are also possible in which an aluminium or other metallic substrate carries an ITO layer, a hole injection layer, a hole transport layer, an electroluminescent layer, an electron transport layer, an electron injection layer and an ITO or other transparent cathode, light being emitted through the cathode. A further possibility is an inverted OLED in which a cathode of aluminium or aluminium alloyed with a low work function metal carries successively an electron injection layer, an electron transport layer, an electroluminescent layer, a hole transport layer, a hole injection layer and an ITO or other transparent conductive anode, emission of light being through the anode. If desired a hole blocking layer may be inserted e.g. between the electroluminescent layer and the electron transport layer. There may also be incorporated a layer of a reflectivity influencing material e.g. copper quinolate, vanadyl oxyquinolate or vanadyl tetraphenoxy phthalocyanine e.g. as described in WO 2007/052083 (Kathirgamanathan et al.) the contents of which are incorporated herein by reference.

OLEDs of the invention include small molecule OLEDs, polymer light emitting diodes (p-OLEDs), OLEDs that emit light by fluorescence, OLEDs that emit light by phosphorescence (PHOLEDs) and OLEDs that emit light by ion fluorescence (rare earth complexes) and include single-colour or multi-colour active or passive matrix displays.

The front and/or rear plates of an OLED may be provided on front and/or rear surfaces with microlenses or microlens arrays e.g. an array of microlenses of organic polymer (e.g. polymethyl methacrylate) printed onto an OLED substrate or plate e.g. a substrate or plate to form a front plate of an OLED, see e.g. Sun et al., Organic light emitting devices with enhanced outcoupling via microlenses fabricated by imprint lithography, *J. Appl. Phys.* 100, 073106 (2006) and WO 2003/007663 (Moler et al., Princeton). Prismatic and lenticular films are available from Microsharp Corporation Limited of Watchfield, Oxfordshire and microlens and prismatic sheeting is available from 3M Corporation.

There may be employed conducting substrates: ITO/glass, transparent metal coatings/glass, ATO, InZnO/glass and on plastics substrates. Conducting polymer coated plastics and glass may be used, for example, as anodes.

Anode

In many embodiments the anode is formed by a layer of tin oxide or indium tin oxide coated onto glass or other transparent substrate. Other materials that may be used include antimony tin oxide and indium zinc oxide. As regards substrates, rigid or flexible transparent plastics materials may be used, preferably materials which are dimensionally stable, impermeable to water (including water vapour) of relatively high Tg. PEN is a preferred material, other materials that may be used including PES, PEEK and PET. The plastics may be coated with a conductive film and may also have a barrier coating to improve resistance to moisture and hence improve service life.

Hole Injection Materials

A single layer may be provided between the anode and the electroluminescent material, but in many embodiments there are at least two layers one of which is a hole injection layer (buffer layer) and the other of which is a hole transport layer, the two layer structure offering in some embodiments improved stability and device life (see U.S. Pat. No. 4,720,432 (VanSlyke et al., Kodak). The hole injection layer may serve to improve the film formation properties of subsequent organic layers and to facilitate the injection of holes into the hole transport layer.

Suitable materials for the hole injection layer which may be of thickness e.g. 0.1-200 nm depending on material and cell type include hole-injecting porphyrinic compounds—see U.S. Pat. No. 4,356,429 (Tang, Eastman Kodak) e.g. zinc phthalocyanine copper phthalocyanine and ZnTpTP, whose formula is set out below:

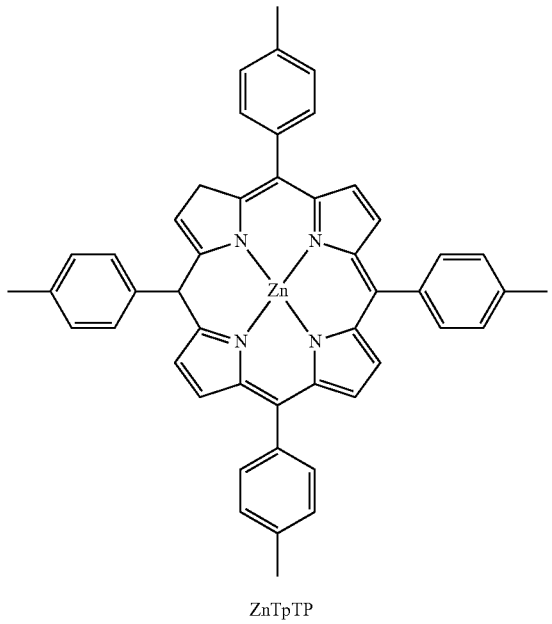

ZnTpTP

Particularly good device efficiencies, turn/on voltages and/or lifetimes may be obtained where the hole injection layer is ZnTpTP both when the host material for the electroluminescent layer is an organic complex e.g. a metal quinolate such as aluminium quinolate and when the host material is an organic small molecule material.

The hole injection layer may also be a fluorocarbon-based conductive polymer formed by plasma polymerization of a fluorocarbon gas—see U.S. Pat. No. 6,208,075 (Hung et al; Eastman Kodak), a triarylamine polymer—see EP-A-0891121 (Inoue et al., TDK Corporation) or a phenylenediamine derivative—see EP-A-1029909 (Kawamura et al., Idemitsu).

Hole-Transport Materials

Hole transport layers which may be used are preferably of thickness 20 to 200 nm.

One class of hole transport materials comprises polymeric materials that may be deposited as a layer by means of spin coating. Such polymeric hole-transporting materials include poly(N-vinylcarbazole) (PVK), polythiophenes, polypyrrole, and polyaniline. Other hole transporting materials are conjugated polymers e.g. poly(p-phenylenevinylene) (PPV) and copolymers including PPV. Other preferred polymers are: poly(2,5 dialkoxyphenylene vinylenes e.g. poly(2-methoxy-5-(2-methoxypentyloxy-1,4-phenylene vinylene), poly(2-methoxypentyloxy)-1,4-phenylenevinylene), poly(2-methoxy-5-(2-dodecyloxy-1,4-phenylenevinylene) and other poly(2,5 dialkoxyphenylenevinylenes) with at least one of the alkoxy groups being a long chain solubilising alkoxy group; polyfluorenes and oligofluorenes; polyphenylenes and oligophenylenes; polyanthracenes and oligoanthracenes; and polythiophenes and oligothiophenes.

A further class of hole transport materials comprises sublimable small molecules. For example, aromatic tertiary amities provide a class of preferred hole-transport materials, e.g. aromatic tertiary amines including at least two aromatic tertiary amine moieties (e.g. those based on biphenyl diamine or of a "starburst" configuration), of which the following are representative:

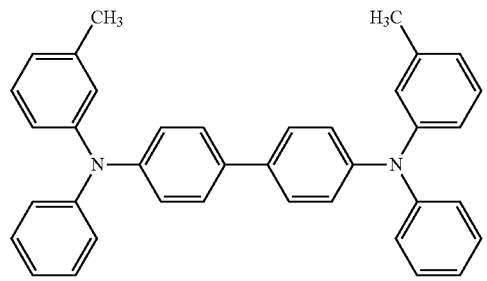

TPD
Tg (° C.) 61
$\mu h$ (cm$^2$ V$^{-1}$ s$^{-1}$) $1 \times 10^{-3}$

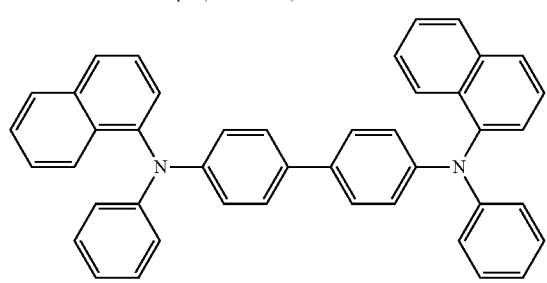

α–NBP
Tg (° C.) 98
$\mu h$ (cm$^2$ V$^{-1}$ s$^{-1}$) $1 \times 10^{-4}$

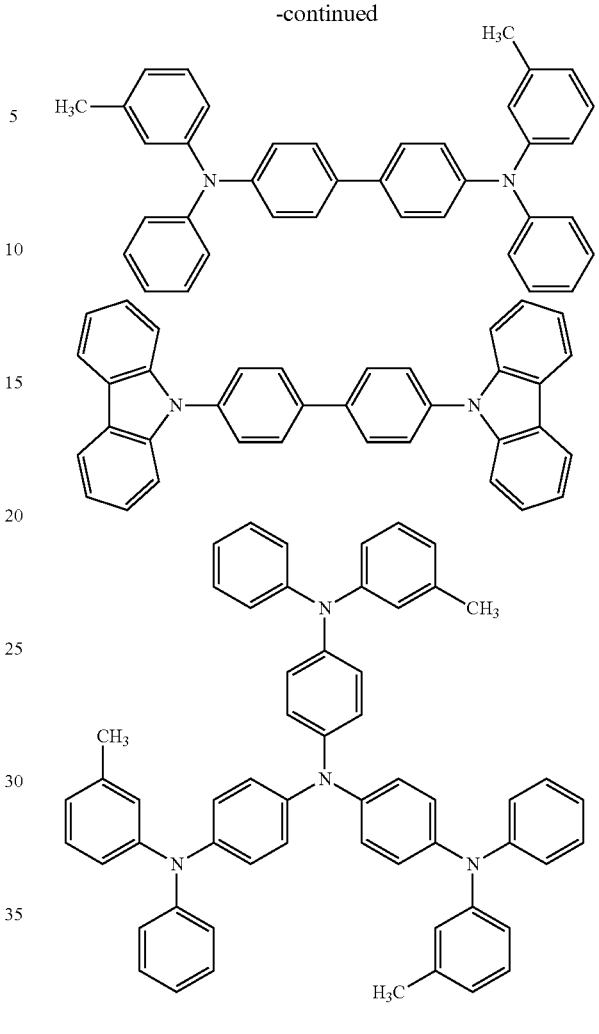

m-MTDATA.
Tg (° C.) 75
$\mu h$ (cm$^2$ V$^{-1}$ s$^{-1}$) $2.7 \times 10^{-5}$

It further includes spiro-linked molecules which are aromatic amines e.g. spiro-TAD (2,2',7,7'-tetrakis-(diphenylamino)-spiro-9,9'-bifluorene).

A further class of small molecule hole transport materials is disclosed in WO 2006/061594 (Kathirgamanathan et al) and is based on diamino dianthracenes. Typical compounds include:
9-(10-(N-(naphthalen-1-yl)-N-phenylamino)anthracen-9-yl)-N-(naphthalen-1-yl)-N-phenylanthracen-10-amine;
9-(10-(N-biphenyl-N-2-m-tolylamino)anthracen-9-yl)-N-biphenyl-N-2-m-tolylamino-anthracen-10-amine; and
9-(10-(N-phenyl-N-m-tolylamino)anthracen-9-yl)-N-phenyl-N-m-tolylanthracen-10-amine.

Electroluminescent Materials

In principle any electroluminescent material may be used, including molecular solids which may be fluorescent dyes e.g. perylene dyes, metal complexes e.g. Alq$_3$, Ir(III)L$_3$, rare earth chelates e.g. Tb(III) complexes, dendrimers and oligomers e.g. sexithiophene, or polymeric emissive materials. The electroluminescent layer may comprise as luminescent material a metal quinolate, iridium, ruthenium, osmium, rhodium, iridium, palladium or platinum complex, a boron complex or a rare earth complex One preferred class of electroluminescent materials comprises host materials doped with dyes which may be fluorescent, phosphorescent or ion-phosphorescent (rare earth). The term "electroluminescent device" includes electrophosphorescent devices.

Preferably the host is doped with a minor amount of a fluorescent material as a dopant, preferably in an amount of 0.01 to 25% by weight of the doped mixture. As discussed in U.S. Pat. No. 4,769,292 (Tang et al., Kodak), the contents of which are included by reference, the presence of the fluorescent material permits a choice from amongst a wide latitude of wavelengths of light emission. In particular, as disclosed in U.S. Pat. No. 4,769,292 by blending with the organo metallic complex a minor amount of a fluorescent material capable of emitting light in response to hole-electron recombination, the hue of the light emitted from the luminescent zone, can be modified. In theory, if a host material and a fluorescent material could be found for blending which have exactly the same affinity for hole-electron recombination, each material should emit light upon injection of holes and electrons in the luminescent zone. The perceived hue of light emission would be the visual integration of both emissions. However, since imposing such a balance of host material and fluorescent materials is limiting, it is preferred to choose the fluorescent material so that it provides the favoured sites for light emission. When only a small proportion of fluorescent material providing favoured sites for light emission is present, peak intensity wavelength emissions typical of the host material can be entirely eliminated in favour of a new peak intensity wavelength emission attributable to the fluorescent material.

While the minimum proportion of fluorescent material sufficient to achieve this effect varies, in no instance is it necessary to employ more than about 10 mole percent fluorescent material, based on host material and seldom is it necessary to employ more than 1 mole percent of the fluorescent material. On the other hand, limiting the fluorescent material present to extremely small amounts, typically less than about $10^{-3}$ mole percent, based on the host material, can result in retaining emission at wavelengths characteristic of the host material. Thus, by choosing the proportion of a fluorescent material capable of providing favoured sites for light emission, either a full or partial shifting of emission wavelengths can be realized. This allows the spectral emissions of the EL devices to be selected and balanced to suit the application to be served. In the case of fluorescent dyes, typical amounts are 0.01 to 5 wt %, for example 2-3 wt %. In the case of phosphorescent dyes typical amounts are 0.1 to 15 wt %. In the case of ion phosphorescent materials typical amounts are 0.01-25 wt % or up to 100 wt %.

Choosing fluorescent materials capable of providing favoured sites for light emission, necessarily involves relating the properties of the fluorescent material to those of the host material. The host can be viewed as a collector for injected holes and electrons with the fluorescent material providing the molecular sites for light emission. One important relationship for choosing a fluorescent material capable of modifying the hue of light emission when present in the host is a comparison of the reduction potentials of the two materials. The fluorescent materials demonstrated to shift the wavelength of light emission have exhibited a less negative reduction potential than that of the host. Reduction potentials, measured in electron volts, have been widely reported in the literature along with varied techniques for their measurement. Since it is a comparison of reduction potentials rather than their absolute values which is desired, it is apparent that any accepted technique for reduction potential measurement can be employed, provided both the fluorescent and host reduction potentials are similarly measured. A preferred oxidation and reduction potential measurement techniques is reported by R. J. Cox, *Photographic Sensitivity*, Academic Press, 1973, Chapter 15.

A second important relationship for choosing a fluorescent material capable of modifying the hue of light emission when present in the host is a comparison of the band-gap potentials of the two materials. The fluorescent materials demonstrated to shift the wavelength of light emission have exhibited a lower band gap potential than that of the host. The band gap potential of a molecule is taken as the potential difference in electron volts (eV) separating its ground state and first singlet state. Band gap potentials and techniques for their measurement have been widely reported in the literature. The band gap potentials herein reported are those measured in electron volts (eV) at an absorption wavelength which is bathochromic to the absorption peak and of a magnitude one tenth that of the magnitude of the absorption peak. Since it is a comparison of band gap potentials rather than their absolute values which is desired, it is apparent that any accepted technique for band gap measurement can be employed, provided both the fluorescent and host band gaps are similarly measured. One illustrative measurement technique is disclosed by F. Gutman and L. E. Lyons, *Organic Semiconductors*, Wiley, 1967, Chapter 5.

With host materials which are themselves capable of emitting light in the absence of the fluorescent material, it has been observed that suppression of light emission at the wavelengths of emission characteristics of the host alone and enhancement of emission at wavelengths characteristic of the fluorescent material occurs when spectral coupling of the host and fluorescent material is achieved, By "spectral coupling" it is meant that an overlap exists between the wavelengths of emission characteristic of the host alone and the wavelengths of light absorption of the fluorescent material in the absence of the host. Optimal spectral coupling occurs when the emission wavelength of the host is within ±25 nm of the maximum absorption of the fluorescent material alone. In practice advantageous spectral coupling can occur with peak emission and absorption wavelengths differing by up to 100 nm or more, depending on the width of the peaks and their hypsochromic and bathochromic slopes. Where less than optimum spectral coupling between the host and fluorescent materials is contemplated, a bathochromic as compared to a hypsochromic displacement of the fluorescent material produces more efficient results.

Useful fluorescent materials are those capable of being blended with the host and fabricated into thin films satisfying the thickness ranges described above forming the luminescent zones of the EL devices of this invention. While crystalline organometallic complexes do not lend themselves to thin film formation, the limited amounts of fluorescent materials present in the host permit the use of fluorescent materials which are alone incapable of thin film formation. Preferred fluorescent materials are those which form a common phase with the host. Fluorescent dyes constitute a preferred class of fluorescent materials, since dyes lend themselves to molecular level distribution in the host. Although any convenient technique for dispersing the fluorescent dyes in the host can be used preferred fluorescent dyes are those which can be vacuum vapour deposited along with the host materials.

One class of host materials comprises metal complexes e.g. metal quinolates such as lithium quinolate, aluminium quinolate, titanium quinolate, zirconium quinolate or hafnium quinolate which may be doped with fluorescent materials or dyes as disclosed in patent application WO 2004/058913.

In the case of quinolates e.g. aluminium quinolate:

(a) the compounds below, for example, can serve as red dopants:

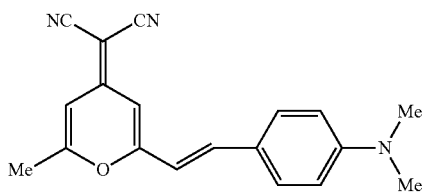
DCM

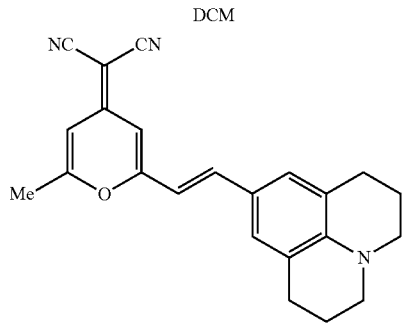
DCJT

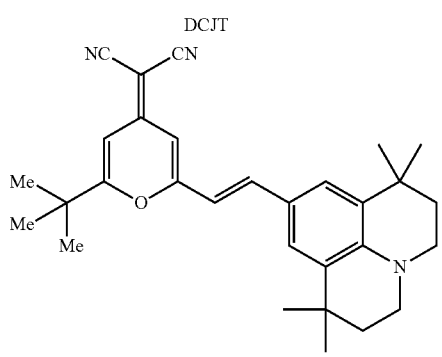
DCJTi

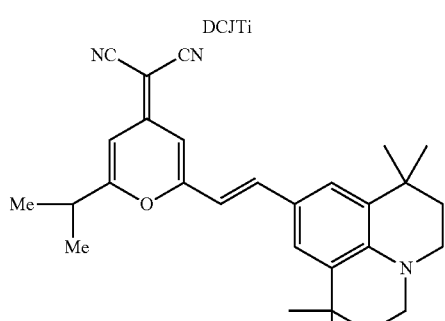
DCJTB (b) the compounds below, for example can serve as green dopants:

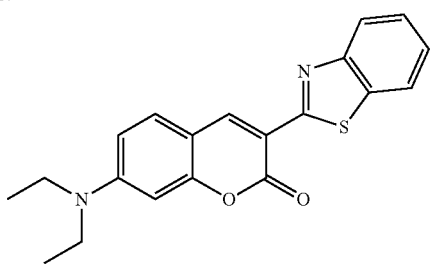

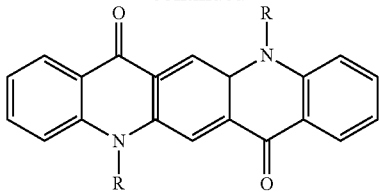

wherein R is $C_1$-$C_4$ alkyl, monocyclic aryl, bicyclic aryl, monocyclic heteroaryl, bicyclic heteroaryl, aralkyl or thienyl, preferably phenyl; and (c) for biphenyloxy aluminium bis-quinolate ($BAlQ_2$) or aluminium quinolate the compounds perylene and 9-(10-(N-(naphthalen-8-yl)-N-phenylamino)anthracen-9-yl)-N-(naphthalen-8-yl)-N-phenylanthracen-10-amine can serve as a blue dopants.

Another preferred class of hosts is small molecules incorporating conjugated aromatic systems with e.g. 4-10 aryl or heteroaryl rings which may bear substituents e.g. alkyl (especially methyl), alkoxy and fluoro and which may also be doped with fluorescent materials or dyes.

An example of a system of the above kind is a blue-emitting material based on the following compound (Compound H) as host

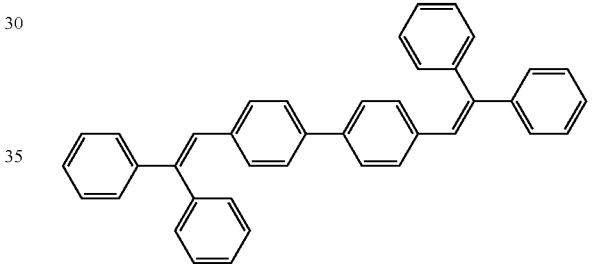

and perylene or 9-(10-(N-(naphthalen-8-yl)-N-phenylamino)anthracen-9-yl)-N-(naphthalen-8-yl)-N-phenylanthracen-10-amine as dopant. Further examples of host materials which are small aromatic molecules are shown below:

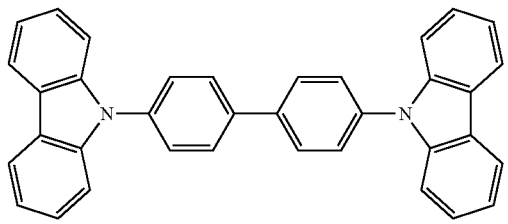
CBP

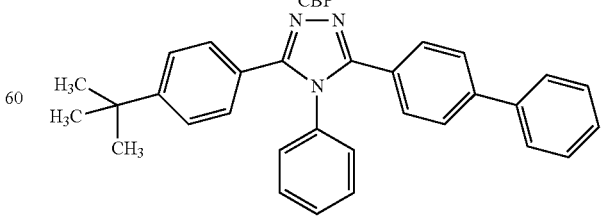
TAZ

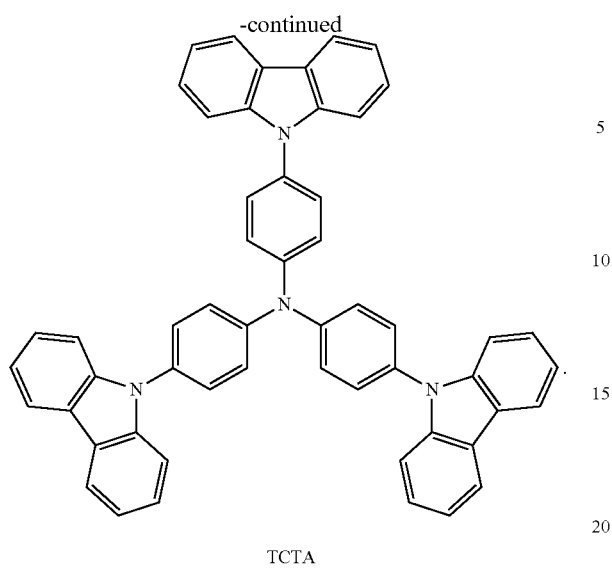

TCTA 2,9-Bis(2-thiophen-2-yl-vinyl)[1,10]phenanthroline may, as explained above, may be used as host in the electroluminescent layer or may be present on its own.

Blue-emitting materials may be based on an organic host (e.g. a conjugated aromatic compound as indicated above) and diarylamine anthracene compounds disclosed in WO 2006/090098 (Kathirgamanathan et al.) as dopants. For example, CBP may be doped with blue-emitting substituted anthracenes inter alia 9,10-bis(-4-methylbenzyl)-anthracene,
9,10-bis-(2,4-dimethylbenzyl)-anthracene,
9,10-bis-(2,5-dimethylbenzyl)-anthracene,
1,4-bis-(2,3,5,6-tetramethylbenzyl)-anthracene,
9,10-bis-(4-methoxybenzyl)-anthracene,
9,10-bis-(9H-fluoren-9-yl)-anthracene,
2,6-di-t-butylanthracene,
2,6-di-t-butyl-9,10-bis-(2,5-dimethylbenzyl)-anthracene,
2,6-di-t-butyl-9,10-bis-(naphthalene-1-ylmethyl)-anthracene.

Further blue-emitting materials may employ TCTA as host and it may be doped with the blue phosphorescent materials set out below, see WO 2005/080526 (Kathirgamanathan et al.):

Blue Phosphorescent Materials

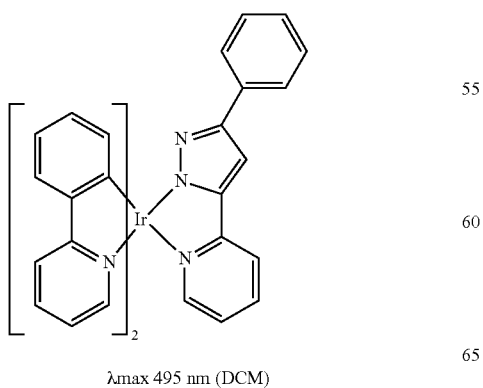

λmax 495 nm (DCM)

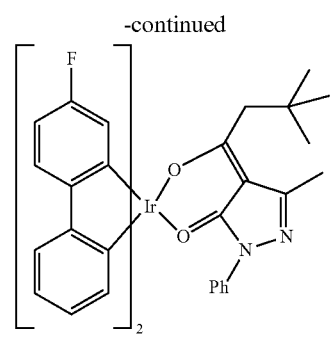

λmax 493 nm (DCM)

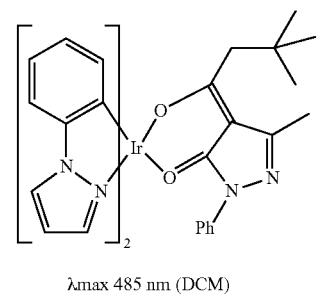

λmax 485 nm (DCM)

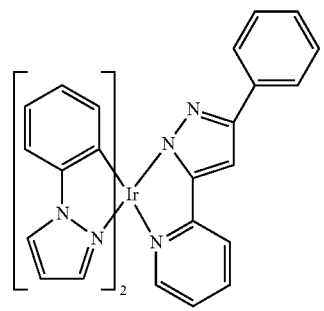

λmax 485 nm (DCM)

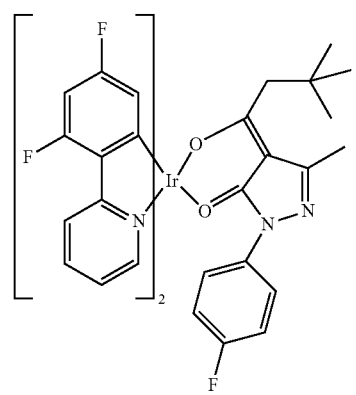

λmax 484 nm (DCM)

-continued
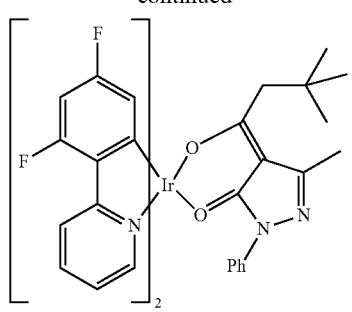
λmax 483 nm (DCM)
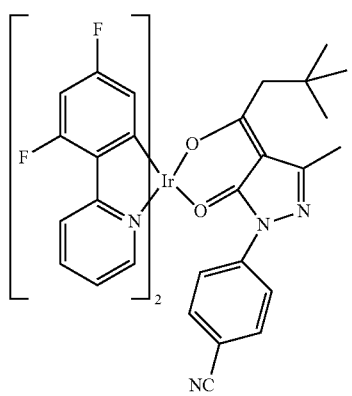
λmax 480 nm (DCM)
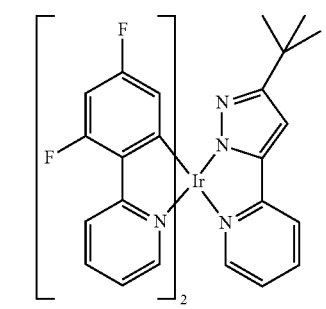
λmax 479 nm (DCM)
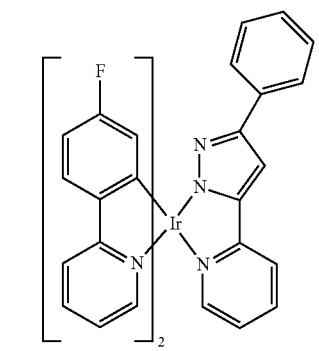
λmax 477 nm (DCM)
-continued
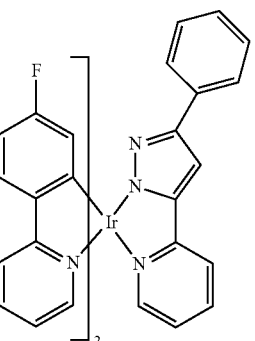
λmax 470 nm (DCM)
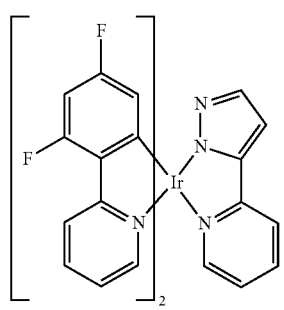
λmax 469 nm, 493 nm (DCM)
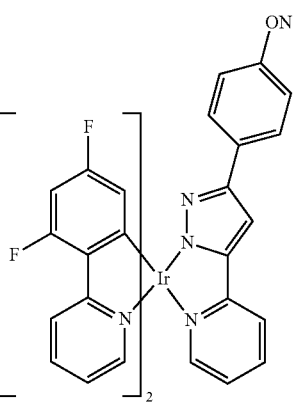
λmax 468 nm (DCM)
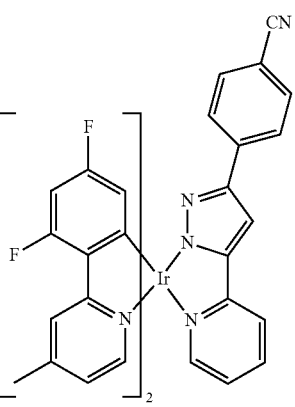
λmax 462 nm (DCM)

Examples of green phosphorescent materials that may be employed with CBP or TAZ are set out below (see WO 2005/080526):
Green Phosphorescent Materials
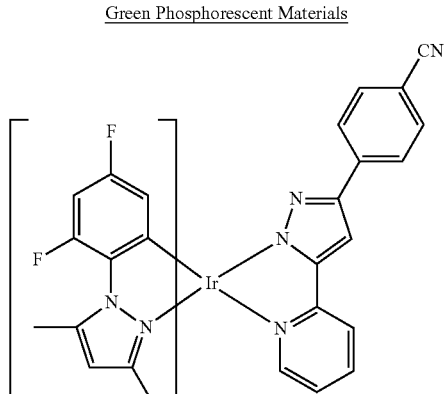
λmax 502 nm (DCM)
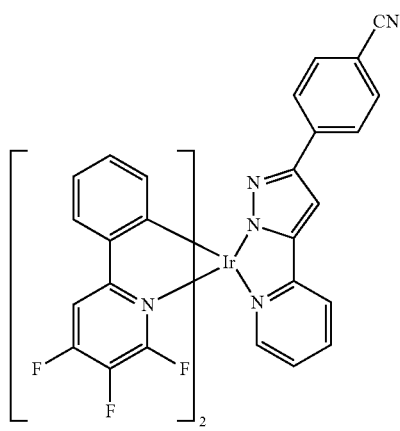
λmax 520 nm (DCM)
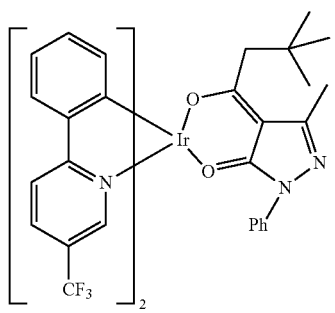
λmax 509 nm (DCM)
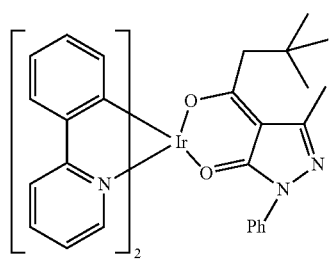
λmax 526 nm (DCM)
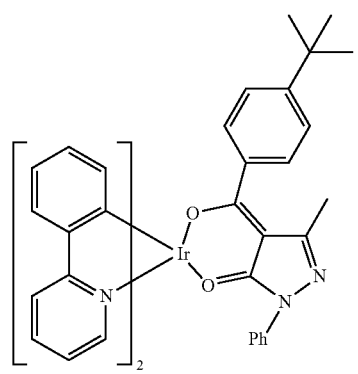
λmax 528 nm (DCM)
Examples of red phosphorescent materials that may be employed with CBP or TAZ are set out below (see WO 2005/080526):
Red Phosphorescent Materials
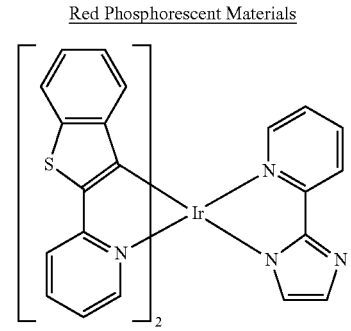
λmax 596 nm (DCM)
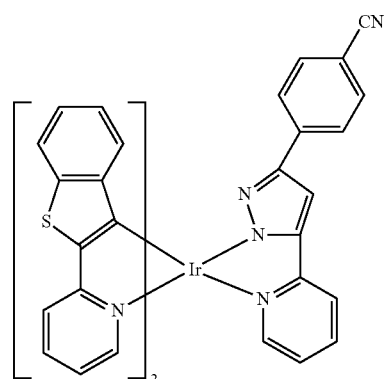
λmax 596 nm (DCM)

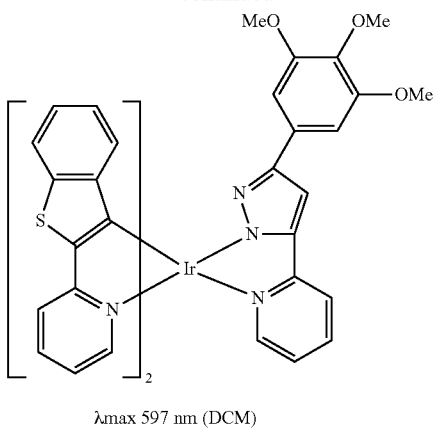

λmax 597 nm (DCM)

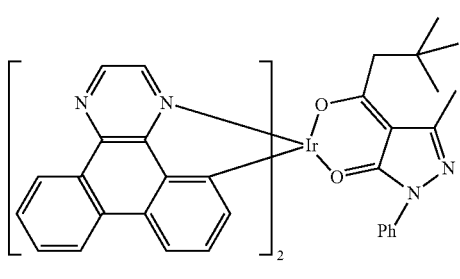

λmax 600 nm (DCM)

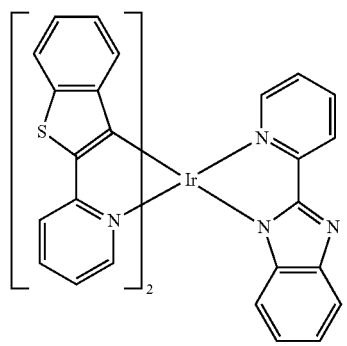

λmax 604 nm (DCM)

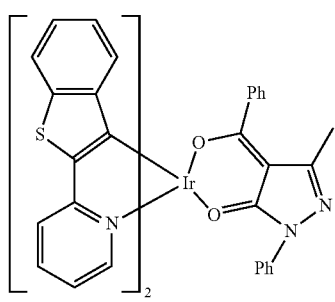

λmax 614 nm (DCM)

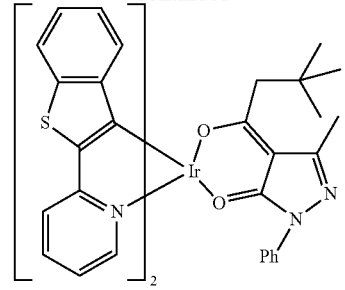

λmax 615 nm (DCM)

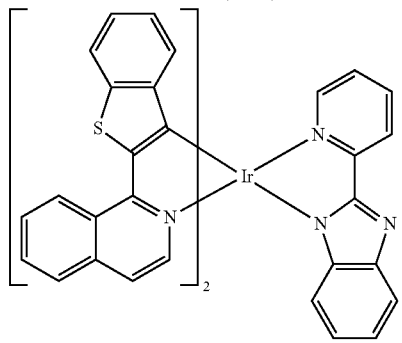

λmax 682 nm (DCM)

As further dopants, fluorescent laser dyes are recognized to be particularly useful fluorescent materials for use in the organic EL devices of this invention. Dopants which can be used include diphenylacridine, coumarins, perylene and their derivatives. Useful fluorescent dopants are disclosed in U.S. Pat. No. 4,769,292. One class of preferred dopants is coumarins. The following are illustrative fluorescent coumarin dyes known to be useful as laser dyes:

FD-1 7-Diethylamino-4-methylcoumarin,
FD-2 4,6-Dimethyl-7-ethylaminocoumarin,
FD-3 4-Methylumbelliferone,
FD-4 3-(2'-Benzothiazolyl)-7-diethylaminocoumarin,
FD-5 3-(2'-Benzimidazolyl)-7-N,N-diethylaminocoumarin,
FD-6 7-Amino-3-phenylcoumarin,
FD-7 3-(2'-N-Methylbenzimidazolyl)-7-N,Ndiethylaminocoumarin,
FD-8 7-Diethylamino-4-trifluoromethylcoumarin,
FD-9 2,3,5,6-1H,4H-Tetrahydro-8-methylquinolazino[9,9a,1-gh]coumarin,
FD-10 Cyclopenta[c]julolindino[9,10-3]-11H-pyran-11-one,
FD-11 7-Amino-4-methylcoumarin,
FD-12 7-Dimethylaminocyclopenta[c]coumarin,
FD-13 7-Amino-4-trifluoromethylcoumarin,
FD-14 7-Dimethylamino-4-trifluoromethylcoumarin,
FD-15 1,2,4,5,3H,6H,10H-Tetrahydro-8-trifluoromethyl[1]benzopyrano[9,9a,1-gh]quinolizin-10-one,
FD-16 4-Methyl-7-(sulfomethylamino)coumarin sodium salt,
FD-17 7-Ethylamino-6-methyl-4-trifluoromethylcoumarin,
FD-18 7-Dimethylamino-4-methylcoumarin,
FD-19 1,2,4,5,3H,6H,10H-Tetrahydro-carbethoxy[1]benzopyrano[9,9a,1-gh]quinolizino-10-one,
FD-20 9-Acetyl-1,2,4,5,3H,6H,10H-tetrahydro[1]benzopyrano[9,9a,1-gh]quinolizino-10-one,
FD-21 9-Cyano-1,2,4,5,3H,6H,10H-tetrahydro[1]benzopyrano[9,9a,1-gh]quinolizino-10-one, FD22 9-(t-Butoxycarbonyl)-1,2,4,5,3H,6H,10H-tetrahydro[1]-benzopyrano-[9,9a,1-gh]quinolizino-10-one,
FD-23 4-Methylpiperidino[3,2-g]coumarin,
FD-24 4-Trifluoromethylpiperidino[3,2-g]coumarin,
FD-25 9-Carboxy-1,2,4,5,3H,6H,10H-tetrahydro[1]benzopyrano[9,9a,1-gh]quinolizino-10-one,
FD-26 N-Ethyl-4-trifluoromethylpiperidino[3,2-g].

Other dopants include salts of bis benzene sulphonic acid (require deposition by spin-coating rather than sublimation) such as

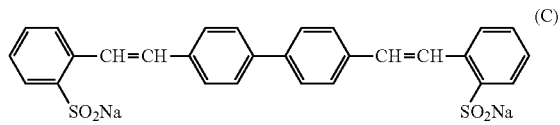

and perylene and perylene derivatives and dopants. Other dopants are dyes such as the fluorescent 4-dicyanomethylene-4H-pyrans and 4-dicyanomethylene-4H-thiopyrans, e.g. the fluorescent dicyanomethylenepyran and thiopyran dyes. Useful fluorescent dyes can also be selected from among known polymethine dyes, which include the cyanines, complex cyanines and merocyanines (i.e. tri-, tetra- and poly-nuclear cyanines and merocyanines), oxonols, hemioxonols, styryls, merostyryls, and streptocyanines. The cyanine dyes include, joined by a methine linkage, two basic heterocyclic nuclei, such as azolium or azinium nuclei, for example, those derived from pyridinium, quinolinium, isoquinolinium, oxazolium, thiazolium, selenazolium, indazolium, pyrazolium, pyrrolium, indolium, 3H-indolium, imidazolium, oxadiazolium, thiadioxazolium, benzoxazolium, benzothiazolium, benzoselenazolium, benzotellurazolium, benzimidazolium, 3H- or 1H-benzoindolium, naphthoxazolium, naphthothiazolium, naphthoselenazolium, naphthotellurazolium, carbazolium, pyrrolopyridinium, phenanthrothiazolium, and acenaphthothiazolium quaternary salts. Other useful classes of fluorescent dyes are 4-oxo-4H-benz-[d,e]anthracenes and pyrylium, thiapyrylium, selenapyrylium, and telluropyrylium dyes.

Further blue-emitting materials are disclosed in the following patents, applications and publications, the contents of which are incorporated herein by reference:

U.S. Pat. No. 5,141,671 (Bryan, Kodak)—Aluminium chelates containing a phenolato ligand and two 8-quinolinolato ligands.

WO 00/32717 (Kathirgamanathan)—Lithium quinolate which is vacuum depositable, and other substituted quinolates of lithium where the substituents may be the same or different in the 2,3,4,5,6 and 7 positions and are selected from alky, alkoxy, aryl, aryloxy, sulphonic acids, esters, carboxylic acids, amino and amido groups or are aromatic, polycyclic or heterocyclic groups.

US 2006/0003089 (Kathirgamanathan)—Lithium quinolate made by reacting a lithium alkyl or alkoxide with 8-hydroxyquinoline in acetonitrile.

Misra, http://www.ursi.org/Proceedings/ProcGA05/pdf/D04.5(01720).pdf Blue organic electroluminescent material bis-(2-methyl 8-quinolinolato) (triphenyl siloxy)aluminium (III) vacuum depositable at $1\times10^{-5}$ Torr.

WO 03/006573 (Kathirgamanathan et al)—Metal pyrazolones.

WO 2004/084325 (Kathirgamanathan et al)—Boron complexes.

WO 2005/080526 (Kathitgamanathan et al)—Blue phosphorescent iridium-based complexes.

Ma et al., *Chem. Comm.* 1998, 2491-2492 Preparation and crystal structure of a tetranuclear zinc(II) compound [$Zn_4O$ $(AID)_6$] with 7-azaindolate as a bridging ligand. Fabrication of inter alia a single-layer LED by vacuum deposition of this compound (<200° C., $2\times10^{-6}$ Torr) onto a glass substrate coated with indium-tin oxide to form a thin homogeneous film was reported.

Further electroluminescent materials which can be used include metal quinolates such as aluminium quinolate, lithium quinolate, titanium quinolate, zirconium quinolate, hafnium quinolate etc.

Many further electroluminescent materials that may be used are disclosed in WO 2004/050793 (pyrazolones), WO 2004/058783 (diiridium metal complexes), WO 2006/016193 (dibenzothiophenyl metal complexes) and WO 2006/024878 (thianthrene metal complexes), see also WO 2006/040593 the contents of which are incorporated herein by reference. Rare earth chelates, in particular may be employed as green and red emitters. Furthermore, there may be used as electroluminescent materials conducting polymers e.g. polyaniline, phenylene vinylene polymers, fluorene homopolymers and copolymers, phenylene polymers, as indicated below:

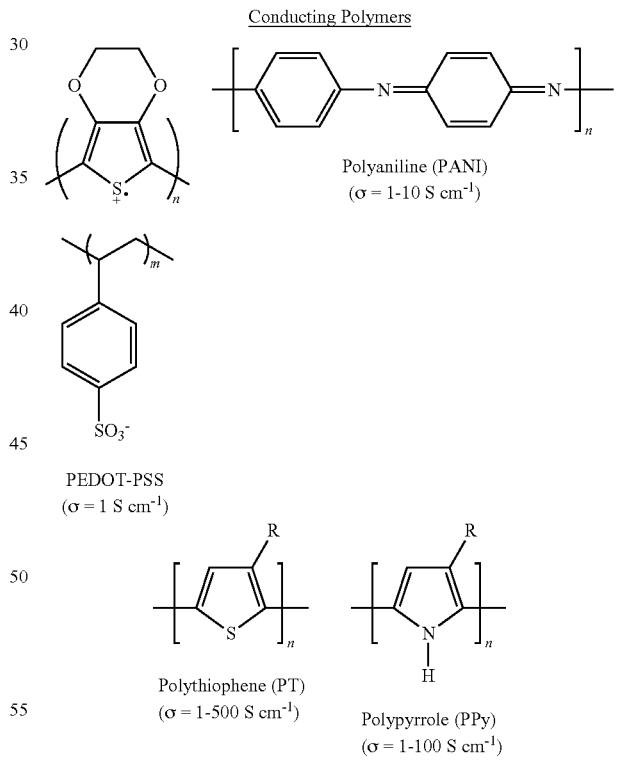

Conducting Polymers

Polyaniline (PANI)
($\sigma = 1\text{-}10$ S cm$^{-1}$)

PEDOT-PSS
($\sigma = 1$ S cm$^{-1}$)

Polythiophene (PT)
($\sigma = 1\text{-}500$ S cm$^{-1}$)

Polypyrrole (PPy)
($\sigma = 1\text{-}100$ S cm$^{-1}$)

Electron Transport Material

Known electron transport materials may be used, including, for example, quinolates.

Aluminium quinolate is thermally and morphologically stable to be evaporated into thin films, easily synthesized and purified and is widely used despite its problems of relatively low mobility, bandgap and tendency to ashing during sublimation. As disclosed in patent application GB 0625541.8 filed 22 Dec. 2006, improved electron transport materials consist of or comprise zirconium or hafnium quinolate, zirconium quinolate being preferred for many embodiments.

Zirconium quinolate has a particularly advantageous combination of properties for use as an electron transport material and which identify it as being a significant improvement on aluminium quinolate for use as an electron transport material. It has high electron mobility. Its melting point (388° C.) is lower than that of aluminium quinolate (414° C.). It can be purified by sublimation and unlike aluminium quinolate it resublimes without residue, so that it is even easier to use than aluminium quinolate. Its lowest unoccupied molecular orbital (LUMO) is at −2.9 eV and its highest occupied molecular orbital (HOMO) is at −5.6 eV, similar to the values of aluminium quinolate. Furthermore, unexpectedly, it has been found that when incorporated into a charge transport layer it slows loss of luminance of an OLED device at a given current with increase of the time for which the device has been operative (i.e. increases device lifetime), or increases the light output for a given applied voltage, the current efficiency for a given luminance and/or the power efficiency for a given luminance. Embodiments of cells in which the electron transport material is zirconium quinolate can exhibit reduced turn-on voltage and up to four times the lifetime of similar cells in which the electron transport material is zirconium quinolate. It is compatible with aluminium quinolate when aluminium quinolate is used as host in the electroluminescent layer of an OLED, and can therefore be employed by many OLED manufacturers with only small changes to their technology and equipment. It also forms a good electrical and mechanical interface with inorganic electron injection layers e.g. a LiF layer where there is a low likelihood of failure by delamination. Of course zirconium quinolate can be used both as host in the electroluminescent layer and as electron transfer layer. The properties of hafnium quinolate are generally similar to those of zirconium quinolate.

Zirconium or hafnium quinolate may be the totality, or substantially the totality of the electron transport layer. It may be a mixture of co-deposited materials which is predominantly zirconium quinolate. The zirconium or hafnium may be doped as described in GB 06 14847.2 filed 26 Jul. 2006, the contents of which are incorporated herein by reference. Suitable dopants include fluorescent or phosphorescent dyes or ion fluorescent materials e.g. as described above in relation to the electroluminescent layer, e.g. in amounts of 0.01-25 wt % based on the weight of the doped mixture. Other dopants include metals which can provide high brightness at low voltage. Additionally or alternatively, the zirconium or hafnium quinolate may be used in admixture with another electron transport material. Such materials may include complexes of metals in the trivalent or pentavalent state which should further increase electron mobility and hence conductivity. The zirconium and hafnium quinolate may be mixed with a quinolate of a metal of group 1, 2, 3, 13 or 14 of the periodic table, e.g. lithium quinolate or zinc quinolate. Preferably the zirconium or hafnium quinolate comprises at least 30 wt % of the electron transport layer, more preferably at least 50 wt %.

Electron Injection Material

The electron injection layer is deposited direct onto the cathode and comprises a Schiff base of one of the above mentioned formulae which may be used alone or in combination with another electron injection material e.g. a quinolate such as lithium or zirconium quinolate. The Schiff base preferably comprises at least 30 wt % of the electron injection layer, more preferably at least 50 wt %.

In the formula set out above, $R_1$ may be polycyclic aryl e.g. naphthyl, anthracenyl, tetracenyl, pentacenyl or a perylene or pyrene compound or may have up to 5 aromatic rings arranged in a chain e.g. biphenyl. It is preferably phenyl or substituted phenyl. $R_2$ and $R_3$ together may form the same groups as $R_1$ and are preferably phenyl or substituted phenyl. Where substituents are present they may be methyl, ethyl, propyl or butyl, including t-butyl substituted, or may be methoxy, ethoxy, propoxy or butoxy including t-butoxy substituted. Particular compounds include

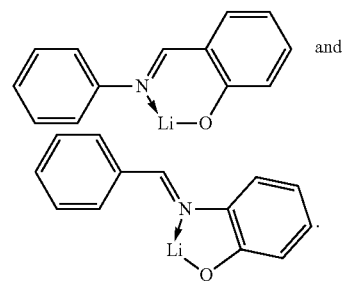

and

A preferred group of compounds is of the formula

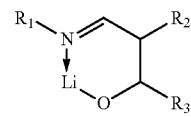

wherein $R_1$ is phenyl or phenyl substituted with one or more $C_1$-$C_4$ alkyl groups e.g. methyl groups and $R_2$ and $R_3$ together form phenyl or phenyl substituted by one or more $C_1$-$C_4$ alkyl groups e.g. methyl groups. These compounds which have N—Li—O in a 6-membered ring have been found to have relatively low vacuum sublimation temperatures, especially when there are methyl substituents. Similar behaviour is expected of compounds of formula:

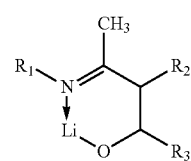

wherein, as previously, $R_1$ is phenyl or phenyl substituted with one or more $C_1$-$C_4$ alkyl groups e.g. methyl groups and $R_2$ and $R_3$ together form phenyl or phenyl substituted by one or more $C_1$-$C_4$ alkyl groups e.g. methyl groups Cathode In many embodiments, aluminium is used as the cathode either on its own or alloyed with elements such as magnesium or silver, although in some embodiments other cathode materials e.g. calcium may be employed. In an embodiment the cathode may comprise a first layer of alloy e.g. Li—Ag, Mg—Ag or Al—Mg closer to the electron injection or electron transport layer and an second layer of pure aluminium further from the electron injection or electron transport layer. Cathode materials may also be on transparent plate materials which may be of glass or may be of plastics which may be rigid or flexible and may be optically transparent. As regards plastics substrates, rigid or flexible transparent plastics materials may be used, preferably materials which are dimensionally stable, impermeable to water (including water vapour) of relatively high Tg. PEN is a preferred material, other materials that may be used including PES, PEEK and PET. The plastics may be coated with a conductive film and may also have a barrier coating to improve resistance to moisture which may be encountered under working conditions e.g. atmospheric moisture.

How the invention may be put into effect will now be described with reference to the following examples.

Preparative Methods

Zirconium tetrakis(8-hydroxyquinolate) (Zrq$_4$)

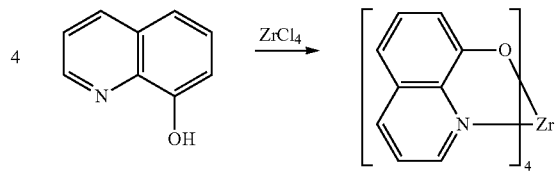

To a solution of 8-Hydroxyquinoline (20.0 g, 138 mmol) in ethanol (300 mL, 95%) was added zirconium (IV) chloride (8.03 g, 34 mmol) in ethanol (50 mL). The pH of the solution was increased by dropwise addition of piperidine (total ~15 mL, 150 mmol) until a yellow precipitate forms. The suspension was heated to approx. 60° for 1 hour, cooled to room temperature and the precipitate collected onto a Buchner funnel. This was thoroughly washed with ethanol (3×100 mL, 95%) and dried under vacuum. Initial purification was performed by Soxhlet extraction with 1,4-dioxane for 24 hours. Concentration of the 1,4-dioxane yields a yellow precipitate, which was collected on a Buchner funnel and washed with ethanol (100 mL, 95%). This sample was dried in a vacuum oven at 80° C. for 4 hours. Final purification was achieved by sublimation. Yield-75% before sublimation. (60% after 2 sublimations). Sublimation (390° C., $10^{-6}$ Torr), m.p. 383° C.

Hafnium tetrakis(8-hydroxyquinolate) (Hfq$_4$)

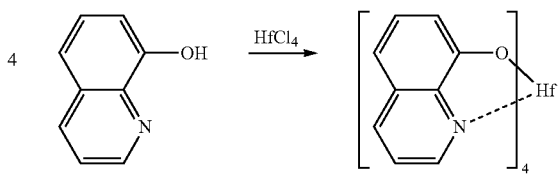

To a solution of 8-Hydroxyquinoline (5.44 g, 37.5 mmol) in ethanol (200 mL, 95%) was added hafnium (IV) chloride (3.0 g, 9.37 mmol) in ethanol (100 mL), followed by a further 300 mL water. The pH of the solution was increased by dropwise addition of piperidine until a yellow precipitate forms. The resulting yellow precipitate was collected and washed with ethanol (100 mL, 95%), water (200 mL) and finally ethanol (100 mL, 95%). The sample was dried under vacuum at 80° C. until no further weight loss was detected. Sublimation (400° C., $10^{-6}$ Torr) yielded an analytical sample (4.5 g, 64%), m.p. 398° C.

1a Synthesis of N-salicylideneaniline

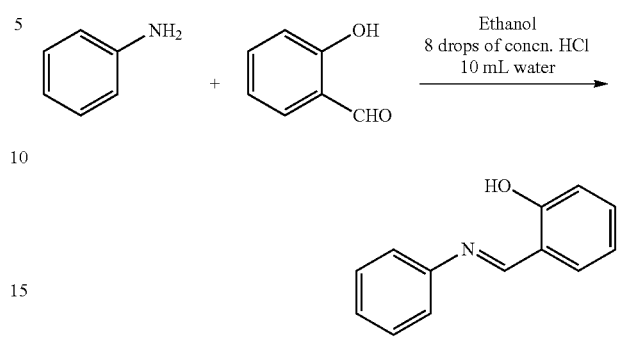

To a mixture of salicylaldehyde (40 mL, 45.84 g, 375.37 mmol)) and aniline (22 mL, 31.72 g, 374.66 mmol), was added ethanol (90 mL), 8 drops of concentrated hydrochloric acid and water (10 mL). This reaction mixture was refluxed for one hour, allowed to cool to room temperature and left in the refrigerator over the weekend. A large quantity of orange solid was formed after 2 hours in the refrigerator. It was filtered off and washed with ethanol. Recrystallisation from ethanol afforded 31.53 g of product.

1b Synthesis of Lithium 2-phenyliminomethyl phenolate (Compound A)

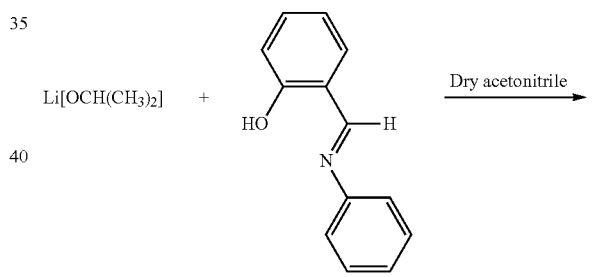

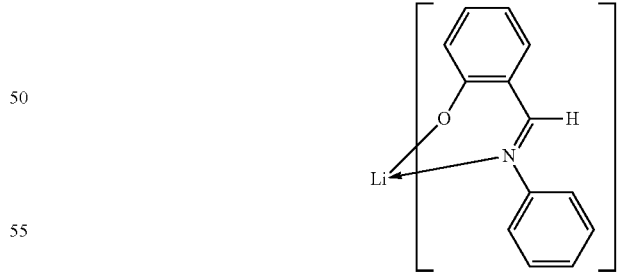

Lithium isopropoxide (300 mL, 20.7 g, 66.03 mmol) was added slowly to a solution of N-salicylideneaniline (61.83 g, 66.03 mmol) in dried acetonitrile (200 mL) under nitrogen atmosphere. A pale yellow precipitate was formed and was left stirring overnight. It was filtered off, washed thoroughly with acetonitrile and dried in vacuum oven for 8 hours at 80° C. Giving 61.6 g of product (97% yield). Sublimation (260° C., $10^{-6}$ Torr.) yielded an analytical sample (25.1 g from 29.2 g).

2a Synthesis of N-salicylidene-2-methylaniline, N-salicylidene-3-methylaniline and N-salicylidene-4-methylaniline

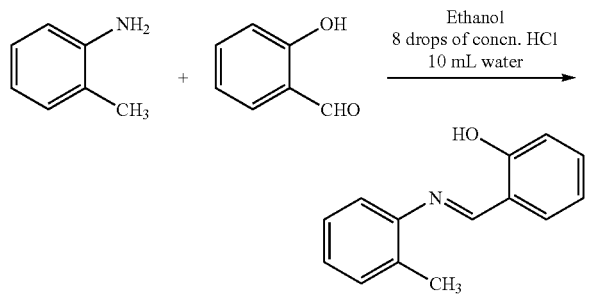

To a mixture of salicylaldehyde (15.00 mL, 17.16 g, 140.76 mmol) and o-toluidine (15.00 mL, 15.06 g, 140.54 mmol), was added ethanol (30 mL), 8 drops of concentrated hydrochloric acid and water (10 mL). This reaction mixture was refluxed for two hours and left vigorously stirred over the weekend at room temperature. The yellow crystalline solid was collected by filtration, recrystallised from ethanol, washed thoroughly with ethanol and dried in vacuum oven for over 8 hours at >40° C., giving 17.24 g of product (58% yield). It gave a bright yellow fluorescence.

N-salicylidene-3-methylaniline and N-salicylidene-4-methylaniline were synthesised using the procedure described above, starting with m-toluidine and p-toluidine, respectively.

2b Synthesis of N-salicylidene-2-methylaniline lithium complex and the corresponding 3-methylaniline and 4-methylaniline complexes

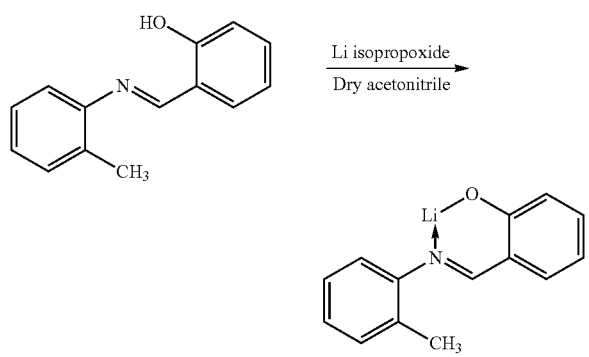

To a stirred solution of N-salicylidene-2-methylaniline (11.00 g, 52.07 mmol) in dry acetonitrile (80 mL), was added lithium isopropoxide (52.00 mL, 3.58 g, 54.34 mmol). A small quantity of white precipitate was slowly formed after 15 minutes of stirring. This reaction mixture was left vigorously stirred overnight at room temperature. The white solid was collected by filtration, washed thoroughly with acetonitrile and dried in vacuum oven for over 8 hours at 80° C. Giving 10.47 g of product (93% yield). Sublimation (235° C., $10^{-6}$ Torr.) yielded an analytical sample (6.5 g from 10.2 g).

The corresponding 3-methyl and 4-methyl compounds were synthesised using the same procedure as described above and using N-salicylidene-3-methylaniline and N-salicylidene-4-methylaniline respectively as starting materials.

3a Synthesis of N-salicylidene-2,3-dimethylaniline, N-salicylidene-2,4-dimethylaniline and N-salicylidene-2,5-dimethylaniline

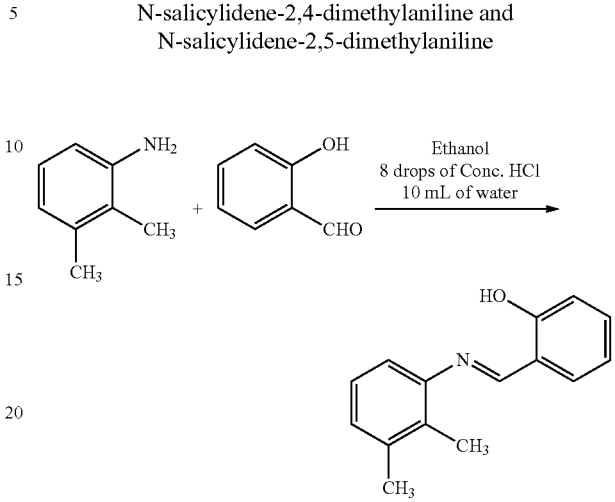

To a mixture of salicylaldehyde (15.00 mL, 17.16 g, 140.76 mmol) and 2,3-dimethylaniline (17.20 mL, 17.08 g, 140.94 mmol), was added ethanol (30 mL), 8 drops of concentrated hydrochloric acid and water (10 mL). This reaction mixture was refluxed for two hours and left vigorously stirred overnight at room temperature. The resulting yellow solid was collected by filtration, recrystallised from ethanol, washed thoroughly with ethanol and dried in vacuum oven for over 8 hours at >40° C., giving 29.98 g of product (95% yield).

N-salicylidene-2,4-dimethylaniline and N-salicylidene-2,5-dimethylaniline were synthesised using the same procedure and using 2,4-dimethylaniline and 2,5-dimethylaniline respectively as starting materials.

3b Synthesis of N-salicylidene-2,3-dimethylaniline lithium complex, N-salicylidene-2,4-dimethylaniline lithium complex and N-salicylidene-2,5-dimethylaniline lithium complex

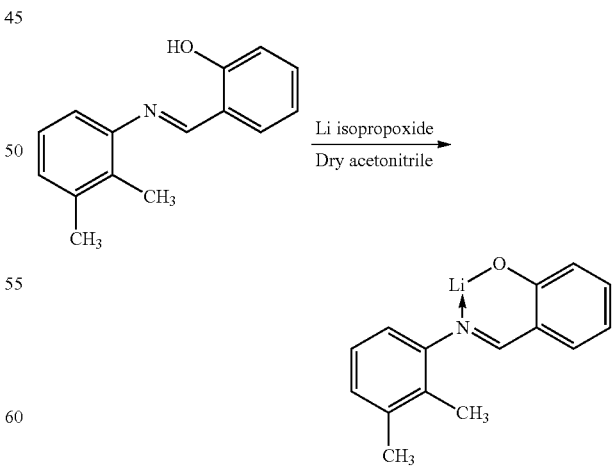

To a stirred solution of N-salicylidene-2,3-dimethylaniline (6.00 g, 26.63 mmol) in dry acetonitrile (30 mL), was added lithium isopropoxide (25.50 mL, 1.76 g, 26.65 mmol). A yellow precipitate was immediately formed, and the reaction mixture was left vigorously stirred overnight at room temperature. The yellow solid was collected by filtration, washed thoroughly with acetonitrile and dried in vacuum oven for over 8 hours at 80° C., giving 4.94 g of product (80% yield), Sublimation (250° C., $10^{-6}$ Torr.) yielded an analytical sample (2.2 g from 3.0 g).

The corresponding 2,4-dimethyl and 2,5-dimethyl complexes were synthesised using the same procedure described and using N-salicylidene-2,4-dimethylaniline and N-salicylidene-2,5-dimethylaniline respectively as starting materials.

4a Synthesis of N-salicylidene-2-cyanoaniline, cyanoaniline and N-salicylidene-4-cyanoaniline

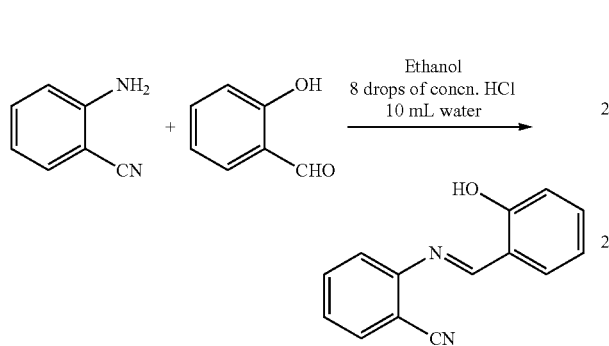

To a mixture of salicylaldehyde (13.5 mL, 15.47 g, 126.61 mmol) and anthranilonitrile (15.00 g, 126.97 mmol), was added ethanol (30 mL), 8 drops of concentrated hydrochloric acid and water (10 mL). This reaction mixture was refluxed for two hours and left stirring at room temperature overnight. The yellow precipitate was filtered, washed with ethanol. The yellow solid was recrystallised from ethanol and left drying in the vacuum oven, giving 19.49 g of product (69% yield).

N-salicylidene-3-cyanoaniline and N-salicylidene-4-cyanoaniline were synthesised using the same procedure and using 3-aminobenzonitrile and 4-aminobenzonitrile respectively as starting materials.

4b Synthesis of
N-salicylidene-2-cyanoanilinelithium complex,
N-salicylidene-3-cyanoanilinelithium complex and
N-salicylidene-4-cyanoanilinelithium complex

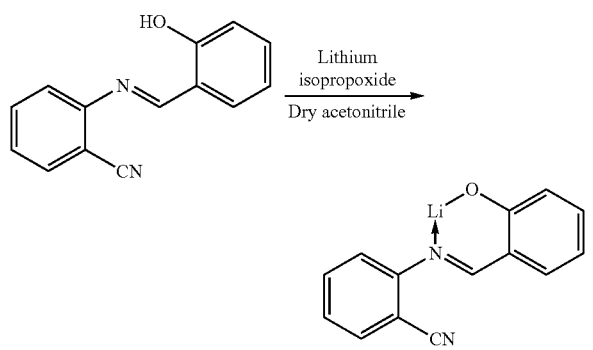

Lithium isopropoxide (44 mL, 3.04 g, 45.98 mmol) was added slowly to a solution of N-salicylidene-2-cyanoaniline (10.00 g, 45.00 mmol) in dried acetonitrile (40 mL) under nitrogen atmosphere. A yellow precipitate was slowly formed and was vigorously stirred for overnight. The yellow precipitate was filtered off, washed thoroughly with acetonitrile and dried in vacuum oven at 80° C. for 8 hours, giving 10.40 g of product (100% yield).

The corresponding 3-cyano and 4-cyano complexes were synthesised using the same procedure and using N-salicylidene-3-cyanoaniline and N-salicylidene-4-cyanoaniline, respectively.

5a Synthesis of N-benzylidene-2-hydroxyaniline

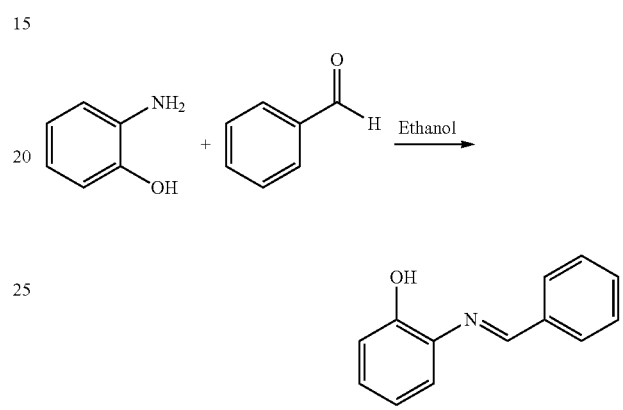

To a solution of 2-aminophenol (28.55 g, 261.61 mmol) in ethanol (40 mL), was added benzaldehyde (30 mL, 31.32 g, 295.14 mmol), and this reaction mixture was refluxed for two hours, and left stirring at room temperature overnight. The creamy white precipitate was filtered, washed with ethanol and dried in vacuum oven at 80° C. for 4 hours. Giving 40.27 g (78% yields).

5b Synthesis of
N-benzylidene-2-hydroxyanilinelithium complex

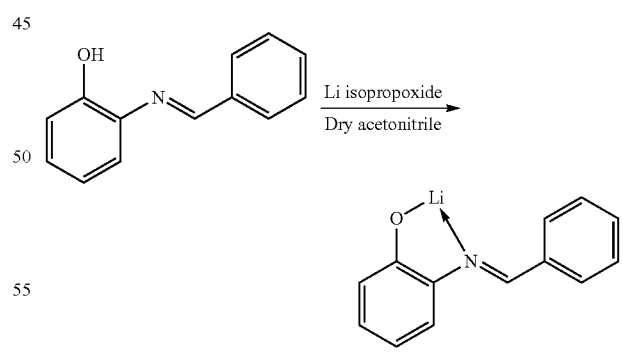

Lithium isopropoxide (50 mL, 3.45 g, 52.25 mmol) was added slowly to a solution of N-benzylicylidene-2-hydroxyaniline (10.25 g, 52.24 mmol) in dried acetonitrile (40 mL) under nitrogen atmosphere. A yellow precipitate was formed and was vigorously stirred for over the weekend. The yellow precipitate was filtered off, washed thoroughly with acetonitrile and dried in vacuum oven at 80° C. for 8 hours, giving 10.55 g of product (100% yield).

6a Synthesis of N-naphthalidene-2-hydroxyaniline

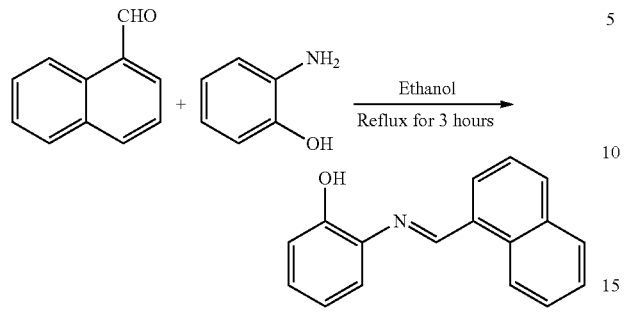

To a stirred solution of 2-aminophenol (14.46 g, 132.54 mmol) in ethanol (30 mL), was added 1-naphthaldehyde (18 mL, 20.7 g, 132.54 mmol). This reaction mixture was refluxed for three hours, and left stirring overnight. The yellowish brown precipitate formed was filtered off, washed with ethanol and dried in vacuum oven at 60° C. for 8 hours, giving 24.34 g of product (74% yields).

6b Synthesis of N-naphthalidene-2-hydroxyanilinelithium complex

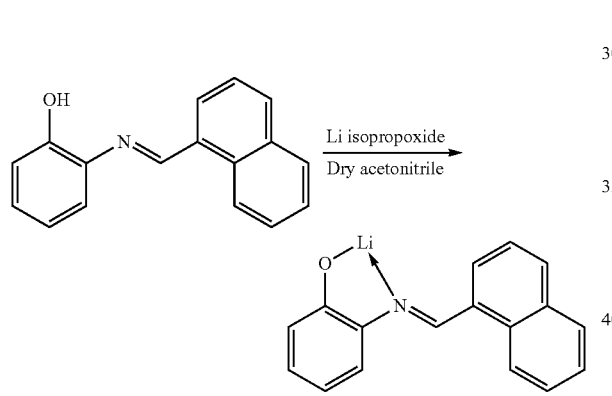

Lithium isopropoxide (20 mL, 1.38 g, 20.90 mmol) was added slowly to a stirred solution of N-naphthalidene-2-hydroxyaniline (5.17 g, 20.91 mmol) in dried acetonitrile (35 mL) under nitrogen atmosphere. This reaction mixture was left stirring overnight. The orange precipitate was collected by filtration, giving 5.12 g of product (97% yield).

7 Synthesis of the N,N'disalicylidene-1,2-phenylenediamino-dilithium complex

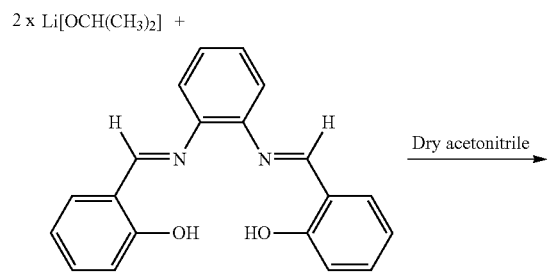

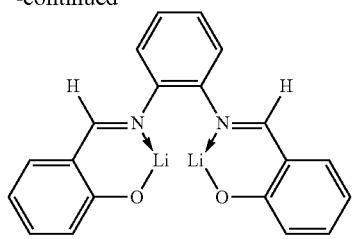

Lithium isopropoxide (50 mL, 3.45 g, 52.25 mmol) was added slowly to a solution of N,N'disalicylidene-1,2-phenylenediamine (8.26 g, 26.11 mmol) in dried acetonitrile (70 mL) under nitrogen atmosphere. A pale yellow precipitate was formed and was left stirring for two hours. The yellow solid was filtered off, washed thoroughly with acetonitrile and dried in vacuum oven for 8 hours at 80° C., giving 2.4 g of product (71% yield). Sublimation (340° C., $10^{-6}$ Torr.) yielded an analytical sample (1.3 g from 2.3 g).

8a Synthesis of Schiff base of thiophene-2-carboxaldehyde with 4-aminophenol[(E)-2-((thiophen-2-yl)methyleneamino)phenol)]

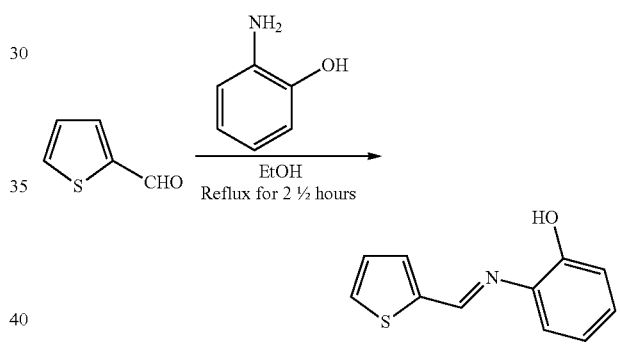

To a dry flask under nitrogen was charged 4-aminophenol (10.0 g, 92 mmol) and ethanol (50 ml). To this was added, with stirring, thiophene-2-carboxaldehyde (11.3 g, 9.4 ml, 0.1 mol). The mixture was heated at reflux (90° C.) for 2.5 hours and subsequently allowed to cool down. The solvent was then removed from the reaction mixture to give a dark brown liquid which was left in a fridge for more than an hour and charged with petroleum ether (40-60° C.). and allowed to solidify. A brown solid was filtered and then slurred with ethanol-pet ether mixture (2:8). Finally, the solid was again filtered, washed with pet ether and dried in vacuo for 18 h. Yield of product (crude): 15.0 g (78%).

8b Synthesis of lithium complex of (E)-2-((thiophen-2-yl)methyleneamino)phenol

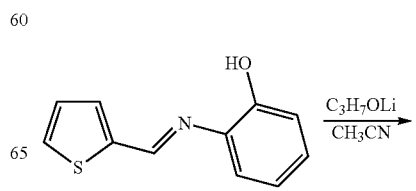

-continued

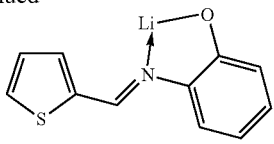

To a dry flask under nitrogen was charged Schiff base (4.0 g, 20 mmol) and dry acetonitrile (50 ml). To this was syringed slowly, with stirring, lithium isopropoxide (1.0M) (1.4 g, 22 ml, 22 mmol). The mixture was left overnight at room temperature while stirring vigorously. A yellow solid was filtered and then slurred with acetonitrile (30 ml). Finally, the solid was again filtered under suction and dried in vacuo for 18 h. Yield of product (crude): 3.8 g (90%).

9a Synthesis of Schiff base of biphenyl-4-carboxaldehyde with 4-aminophenol[2-(biphenyl-4-yl-methyleneamino)phenol]

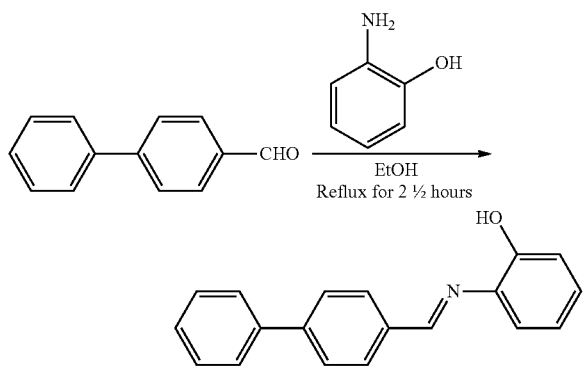

To a dry flask under nitrogen was charged 4-aminophenol (5.0 g, 46 mmol) and ethanol (50 ml). To this was added, with stirring, biphenyl-4-carboaldehyde (8.4 g, 46 mmol). The mixture was heated at reflux (90° C.) for 2½ hours and subsequently allowed to cool down. Filtration gave a yellow solid, which was then slurred with ethanol-pet ether mixture (1:1). Finally, the solid was again filtered, washed with pet ether and dried in vacuo for 18 h. Yield of product (crude): 10.3 g (80%).

9b Synthesis of lithium complex of Schiff base of 2-aminothiazole with salicyladehyde

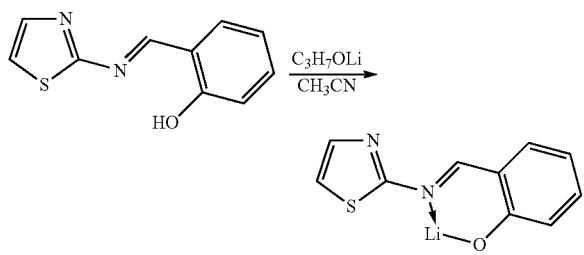

To a dry flask under nitrogen was charged Schiff base (4.0 g, 20 mmol) and dry acetonitrile (50 ml). To this was syringed slowly, with stirring, lithium isopropoxide (1.0M) (1.4 g, 22 ml, 22 mmol). The mixture was left overnight at room temperature while stirring vigorously. A brown solid was filtered and then slurred with acetonitrile (30 ml). Finally, the solid was again filtered under suction and dried in vacuo for 18 h. Yield of product (crude): 3.7 g (85%).

10a Synthesis of Schiff base of 2-aminothiazole with salicyladehyde (2-[(E)-(thiazol-2-ylimino)methyl)phenol]

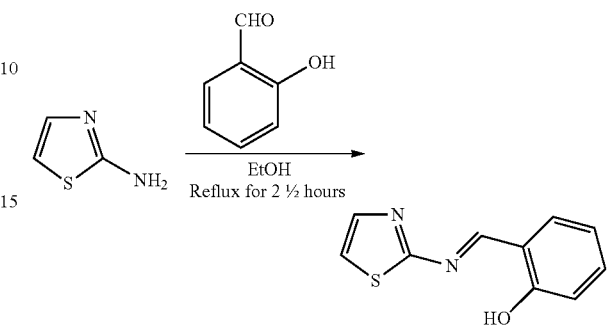

To a dry flask under nitrogen was charged 2-aminothiazole (5.0 g, 50 mmol) and ethanol (50 ml). To this was added, with stirring, salicyladehyde (6.1 g, 5.3 ml, 50 mol). The mixture was heated at reflux (90° C.) for 2.5 hours and subsequently allowed to cool down. The solvent then removed from the reaction mixture resulting in a dark brown liquid which was left in a fridge for more than an hour and charged with petroleum ether (40-60° C.), after which a greenish-yellow solid formed and was filtered and then slurred with ethanol-pet ether mixture (2:8). Finally, the solid was again filtered, washed with pet ether and dried in vacuo for 18 h. Yield of product (crude): 6.0 g (60%).

10b Synthesis of lithium complex of Schiff base of 2-aminothiazole with salicyladehyde

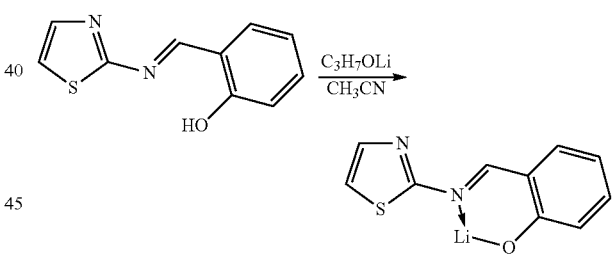

To a dry flask under nitrogen was charged Schiff base (4.0 g, 20 mmol) and dry acetonitrile (50 ml). To this was syringed slowly, with stirring, lithium isopropoxide (1.0M) (1.4 g, 22 ml, 22 mmol). The mixture was left overnight at room temperature while stirring vigorously. A brown solid was filtered and then slurred with acetonitrile (30 ml). Finally, the solid was again filtered under suction and dried in vacuo for 18 h. Yield of product (crude): 3.7 g (85%).

Figure 13:
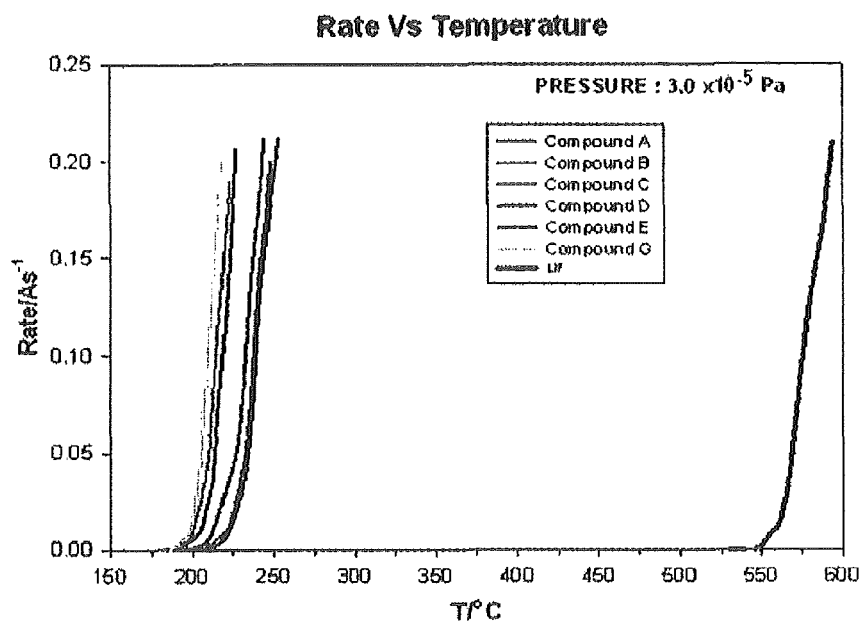
FIG. 13 is a graph showing rate of vacuum sublimation as a function of temperature for compounds of the invention and for lithium fluoride.

Properties of lithium compounds synthesized as described above are given in the accompanying Table. Vacuum sublimation temperatures of some of the compounds are shown in FIG. 13. It will be noted that all the compounds tested exhibit vacuum sublimation temperatures <250° C., whereas LiF exhibits a vacuum sublimation temperatures >550° C. The low vacuum sublimation temperature exhibited by some of the compounds of the invention coupled with their electron injection properties is of significant advantage in device manufacture since thermal effects on already deposited layers are reduced.

| Name | Structure | E.A. (%) Theory | E.A. (%) Found | M. Pt. DSC Peak (°C.) | Mass Spec | Tg (°C.) | UV-Vis. λ_max (nm) Solution | FL. λ_max (nm) Solution | Comments |
|---|---|---|---|---|---|---|---|---|---|
| Compound A | 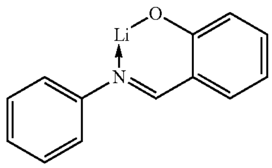 | C = 76.85 H = 4.96 N = 6.89 | C = 77.05 H = 4.90 N = 6.98 | 299 | 1) 203 2) 406 3) 617 4) 820 | No Tg | 341 | 403 472 | Vacuum Processable |
| Compound B | 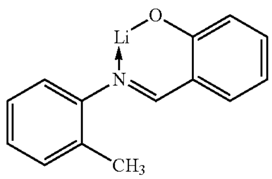 | C = 77.42 H = 5.57 N = 6.45 | C = 77.46 H = 5.54 N = 6.55 | 252 | 1) 217 2) 434 3) 651 | No Tg | 341 | 368 416 506 | Vacuum Processable |
| Compound C | 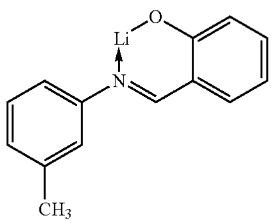 | C = 77.42 H = 5.57 N = 6.45 | C = 76.88 H = 5.37 N = 6.34 | 247 | To be determined | No Tg | 341 | 366 421 497 | Vacuum Processable |
| Compound D | 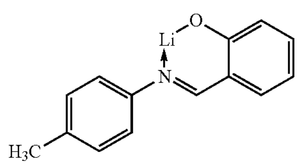 | C = 77.42 H = 5.57 N = 6.45 | C = 77.23 H = 5.50 N = 6.39 | 329 | To be determined | No Tg | 343 | 367 443 505 | Vacuum Processable |
| Compound E | 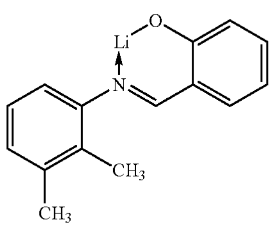 | C = 77.92 H = 6.10 N = 6.06 | C = 78.03 H = 6.12 N = 6.18 | 283 | To be determined | 111 | 340 | 363 429 500 | Vacuum Processable |
| Compound F | 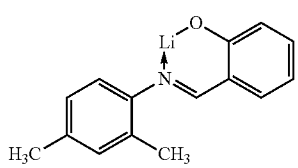 | C = 77.92 H = 6.10 N = 6.06 | C = 78.11 H = 6.08 N = 5.99 | 259 | To be determined | 95 | 346 | 371 424 505 | Vacuum Processable |
| Compound G | 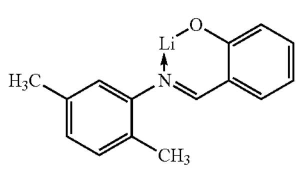 | C = 77.92 H = 6.10 N = 6.06 | C = 78.08 H = 6.11 N = 6.14 | 245 | To be determined | No Tg | 342 | 366 423 507 | Vacuum Processable |
| Compound I | 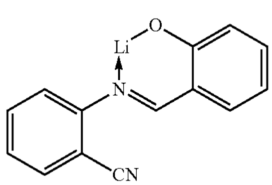 | C = 73.69 H = 3.98 N = 12.28 | C = 73.18 H = 3.81 N = 12.12 | 307 | To be determined | No Tg | Not measured | Not measured | Solution Processable |

-continued

| Name | Structure | E.A. (%) Theory | E.A. (%) Found | M. Pt. DSC Peak (° C.) | Mass Spec | Tg (° C.) | UV-Vis. $\lambda_{max}$ (nm) Solution | FL. $\lambda_{max}$ (nm) Solution | Comments |
|---|---|---|---|---|---|---|---|---|---|
| Compound J | 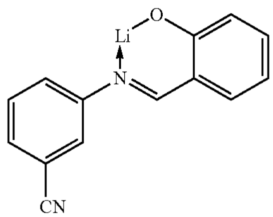 | C = 73.69<br>H = 3.98<br>N = 12.28 | C = 72.65<br>H = 3.75<br>N = 11.98 | 290 | To be determined | 141 | Not measured | Not measured | Solution Processable |
| Compound K | 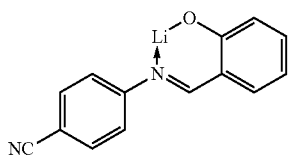 | C = 73.69<br>H = 3.98<br>N = 12.28 | C = 68.39<br>H = 4.53<br>N = 11.07 | 147 | To be determined | No Tg | Not measured | Not measured | Solution Processable |
| Compound L | 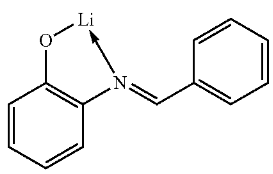 | C = 76.85<br>H = 4.96<br>N = 6.89 | C = 77.00<br>H = 5.29<br>N = 6.78 | 324 | 1) 210<br>2) 413<br>3) 617<br>4) 820 | No Tg | 355 | 381<br>493 | Vacuum & Solution Processable |
| Compound M | 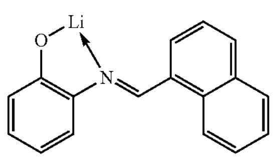 | C = 80.63<br>H = 4.78<br>N = 5.53 | C = 80.07<br>H = 4.77<br>N = 5.45 | 285 | 1) 253<br>2) 525<br>3) 787 | 156 | 364 | 394 | Vacuum & Solution Processable |
| Compound N | 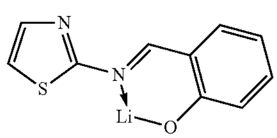 | C = 57.14<br>H = 3.36<br>N = 13.33 | C = 57.80<br>H = 3.07<br>N = 13.13 | 355 | To be determined | No Tg | Not measured | Not measured | Solution Processable |
| Compound O | 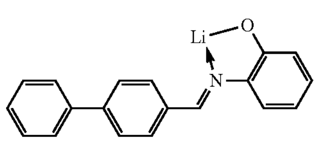 | C = 81.72<br>H = 5.05<br>N = 5.02 | C = 80.08<br>H = 4.93<br>N = 4.88 | 389 | To be determined | No Tg | Not measured | Not measured | Solution Processable |
| Compound P | 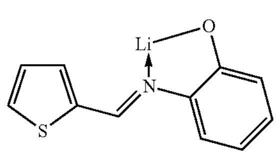 | C = 63.16<br>H = 3.85<br>N = 6.70 | C = 59.39<br>H = 3.85<br>N = 6.21 | 336 | To be determined | No Tg | Not measured | Not measured | Solution Processable |
| Compound Q | 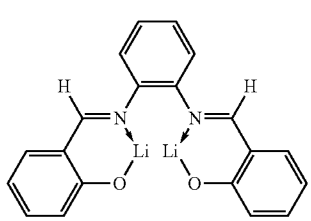 | C = 73.19<br>H = 4.30<br>N = 8.54 | C = 72.42<br>H = 4.10<br>N = 8.41 | ~405 | 1) 328<br>2) 656<br>3) 984 | No Tg | 387 | 462 | Vacuum & Solution Processable |

Device Structure

A pre-etched ITO coated glass piece (10×10 cm²) was used. The device was fabricated by sequentially forming layers on the ITO, by vacuum evaporation using a Solciet Machine, ULVAC Ltd. Chigasaki, Japan. The active area of each pixel was 3 mm by 3 mm. The coated electrodes were encapsulated in an inert atmosphere (nitrogen) with UV-curable adhesive using a glass back plate. Electroluminescence studies were performed with the ITO electrode was always connected to the positive terminal. The current vs. voltage studies were carried out on a computer controlled Keithly 2400 source meter.

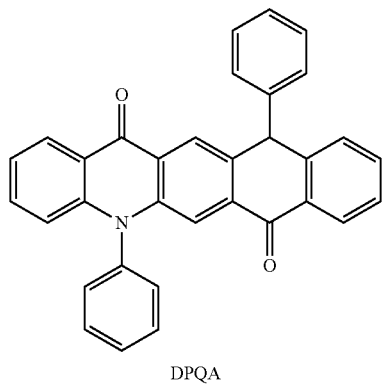

DPQA

Example 1

Devices with green emitters were formed by the method described above consisting of an anode layer, buffer layer, hole transport layer, electroluminescent layer (doped metal complex), electron transport layer, electron injection layer and cathode layer, film thicknesses being in nm:

ITO/ZnTp TP (20)/α-NBP(50)/Alq$_3$:DPQA (40:0.1)/Zrq$_4$ (20)/EIL(0.5)/Al wherein DPQA is diphenyl quinacridone and EIL is the electron injection layer and is LiF or is Compound A.

Compared to cells in which the EIL was LiF, that using Compound A showed greater luminance, greater current and power efficiencies for a given luminance and greater current density for a given applied voltage (FIGS. 1-4). In green-emitting OLEDs compound A also gives better results than lithium quinolate when used as an electron injection layer and evaporates below 300° C.

Example 2

Further devices in which the electron injection layer was a compound made as described above were manufactured and evaluated in relation to similar devices made using Lif as the injection layer. Performance results are shown in FIGS. 5-12. Compounds H and Cz1 used in the electroluminescent layer in some tests are shown below:

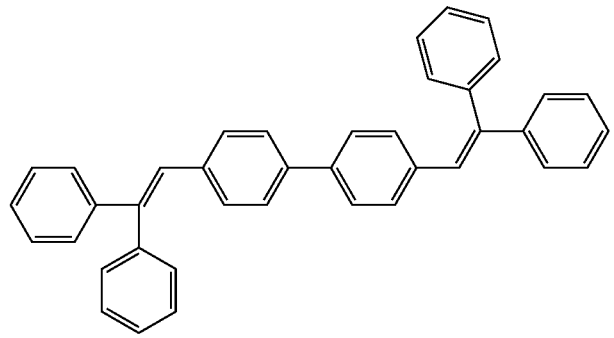

Compound H

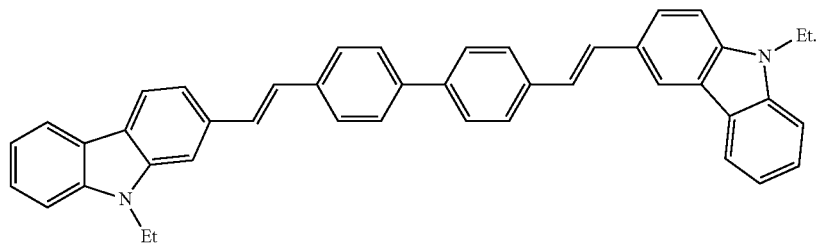

Compound Cz 1

The invention claimed is:

1. A composition comprising a compound of the formula

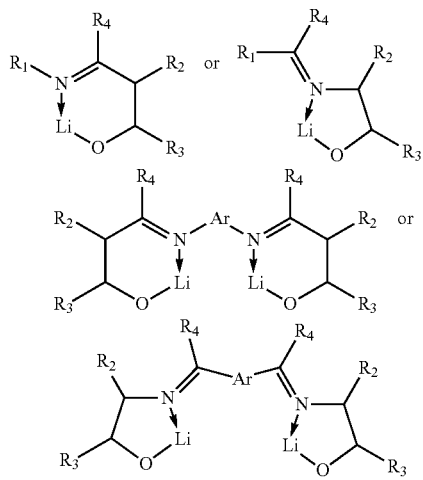

wherein $R_1$ is a 1-5 ring aryl, aralkyl or heteroaryl group which is optionally substituted with one or more $C_1$-$C_4$ alkyl, alkoxy or cyano;

$R_2$ and $R_3$ together form a 1-5 ring aryl, aralkyl or heteroaryl group which is optionally substituted with $C_1$-$C_4$ alkyl, alkoxy or cyano;

$R_4$ is hydrogen, $C_1$-$C_4$ alkyl or aryl; and

Ar is monocyclic, bicyclic or tricyclic aryl or heteroaryl which is optionally substituted with one or more $C_1$-$C_4$-alkyl or alkoxy groups and another organic semiconductor material or a metal.

2. The composition of claim 1, wherein the compound is doped with a metal.

3. The composition of claim 1, wherein the compound as is mixed with an electron transport material.

4. The composition of claim 3, wherein the electron transport material is a metal quinolate or substituted quinolate.

5. The composition of claim 1, wherein the compound is doped with a fluorescent dopant.

6. The composition of claim 1, wherein the compound is doped with a phosphorescent dopant.

7. The composition of claim 1, wherein the compound is doped with a rare earth chelate.

8. A composition comprising the compound the formula

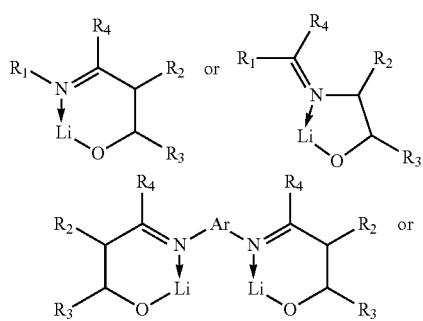

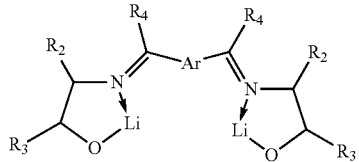

wherein $R_1$ is a 1-5 ring aryl, aralkyl or heteroaryl group which is optionally substituted with one or more $C_1$-$C_4$ alkyl, alkoxy or cyano;

$R_2$ and $R_3$ together form a 1-5 ring aryl, aralkyl or heteroaryl group which is optionally substituted with $C_1$-$C_4$ alkyl, alkoxy or cyano;

$R_4$ is hydrogen, $C_1$-$C_4$ alkyl or aryl; and

Ar is monocyclic, bicyclic or tricyclic aryl or heteroaryl which is optionally substituted with one or more $C_1$-$C_4$-alkyl or alkoxy groups, and an organic solvent.

9. An optical light emitting diode device having a first electrode, a layer comprising a compound or an oligomer and a second electrode, wherein the compound or oligomer is of the formula

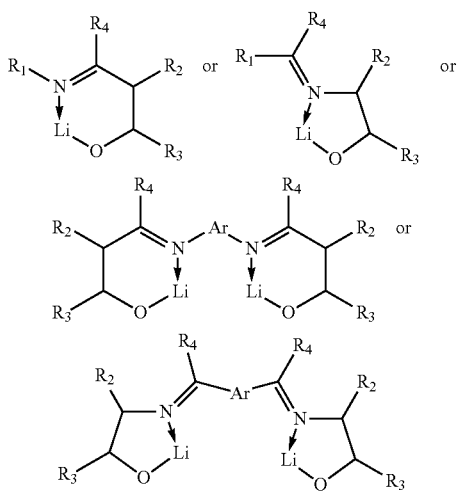

wherein $R_1$ is a 1-5 ring aryl, aralkyl or heteroaryl group which is optionally substituted with one or more $C_1$-$C_4$ alkyl, alkoxy or cyano;

$R_2$ and $R_3$ together form a 1-5 ring aryl, aralkyl or heteroaryl group which is optionally substituted with $C_1$-$C_4$ alkyl, alkoxy or cyano;

$R_4$ is hydrogen, $C_1$-$C_4$ alkyl or aryl; and

Ar is monocyclic, bicyclic or tricyclic aryl or heteroaryl which is optionally substituted with one or more $C_1$-$C_4$-alkyl or alkoxy groups.

10. The device of claim 9, wherein $R_1$ is phenyl or substituted phenyl and $R_2$ and $R_3$ together form phenyl or substituted phenyl.

11. The device of claim 9, which is of formula $$\begin{array}{c} R_1\diagdown N\diagup\diagdown R_2 \\ \quad \downarrow \quad | \\ Li\cdots O\diagdown R_3 \end{array}$$

wherein $R_1$ is phenyl or phenyl substituted with one or more $C_1$-$C_4$ alkyl groups and $R_2$ and $R_3$ together form phenyl or phenyl substituted by one or more $C_1$-$C_4$ alkyl groups.

12. The device of claim 11, wherein $R_1$ and/or $R_2$ and $R_3$ represent phenyl substituted with one or more methyl groups.

13. The device of claim 11, wherein the compound is selected from the following:

[structures]

14. The device of claim 11, wherein the compound is selected from the following:

[structures]

15. The device of claim 9, wherein the compound is selected from the following:

[structures]

16. The device of claim 9, wherein the compound is

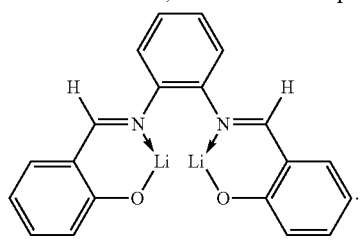

17. The device of claim 9, wherein the second electrode is a cathode and said layer is an electron injection layer located on said cathode.

18. The device of claim 17, which further comprises an electron transport layer between the electron injection layer and an electroluminescent layer, said electroluminescent layer comprising a metal complex.

19. The device of claim 18, wherein the electroluminescent layer comprises lithium, zirconium or hafnium quinolate as host material doped with a dopant.

20. The device of claim 18, wherein the electroluminescent layer comprises aluminium quinolate as the host material doped with a dopant.

21. The device of claim 18, wherein the electroluminescent layer comprises an aromatic tertiary amine as host material doped with a dopant.

22. The device of claim 18, wherein the electroluminescent layer comprises a light emitting material which is a metal or metalloid complex.

23. The device of claim 18, wherein the electroluminescent layer comprises as luminescent material, a metal quinolate, an iridium, ruthenium, osmium, rhodium, iridium, palladium or platinum complex, a boron complex or a rare earth complex or dendrimers of said metal complexes.

24. The device of claim 22, wherein the electroluminescent layer comprises as electroluminescent material, lithium quinolate or aluminium quinolate.

25. The device of claim 18, wherein the electroluminescent layer comprises a light-emitting conjugated polymer or copolymer or a dendrimer.

26. The device of claim 18, having a hole injection layer comprising

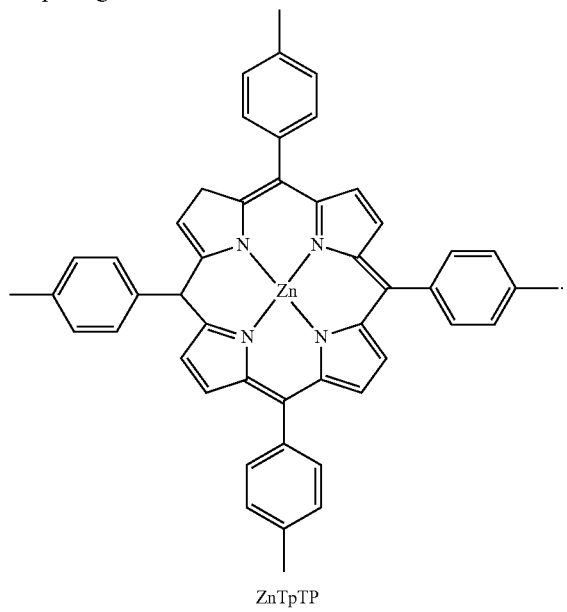

ZnTpTP

27. The device of claim 18, having a hole transport layer comprising α-NBP

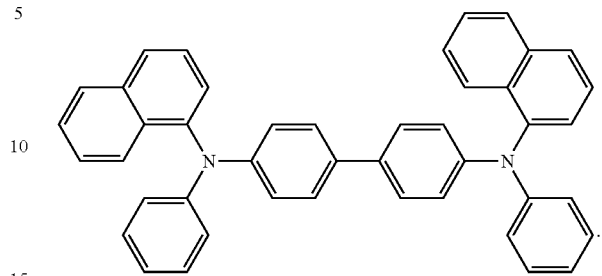

28. An electro-optical or opto-electronic device having a layer comprising the formula

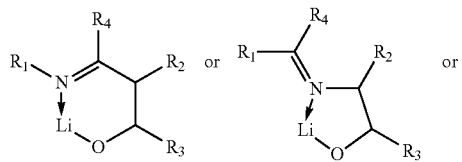

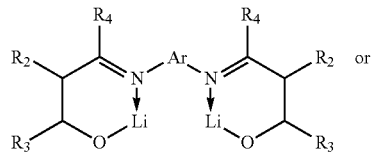

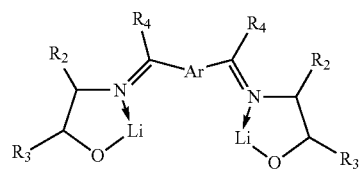

wherein $R_1$ is a 1-5 ring aryl, aralkyl or heteroaryl group which is optionally substituted with one or more $C_1$-$C_4$ alkyl, alkoxy or cyano;

$R_2$ and $R_3$ together form a 1-5 ring aryl, aralkyl or heteroaryl group which is optionally substituted with $C_1$-$C_4$ alkyl, alkoxy or cyano;

$R_4$ is hydrogen, $C_1$-$C_4$ alkyl or aryl; and

Ar is monocyclic, bicyclic or tricyclic aryl or heteroaryl which is optionally substituted with one or more $C_1$-$C_4$-alkyl or alkoxy groups.

29. The device of claim 28, wherein the device is a flat panel display.

30. The device of claim 28, wherein the device is an imaging member for creation of an electrostatic latent image.

* * * * *